United States Patent [19]

Erdman

[11] Patent Number: 5,542,421
[45] Date of Patent: *Aug. 6, 1996

[54] METHOD AND APPARATUS FOR CARDIOVASCULAR DIAGNOSIS

[75] Inventor: Frank H. Erdman, Newtown Square, Pa.

[73] Assignee: Frederick Erdman Association, Havertown, Pa.

[ * ] Notice: The term of this patent shall not extend beyond the expiration date of Pat. No. 5,542,421

[21] Appl. No.: 297,899

[22] Filed: Aug. 30, 1994

Related U.S. Application Data

[63] Continuation-in-part of Ser. No. 922,780, Jul. 31, 1992, Pat. No. 5,365,924.

[51] Int. Cl.⁶ .................................................. A61B 5/00
[52] U.S. Cl. ........................... 128/633; 128/691; 128/665
[58] Field of Search .................. 128/633, 664–6, 128/736, 748, 690, 691, 687, 632, 774

[56] References Cited

U.S. PATENT DOCUMENTS

| H1039 | 4/1992 | Tripp, Jr. et al. | 128/206.28 |
|---|---|---|---|
| Re. 33,834 | 3/1992 | Warner | 128/668 |
| 3,461,865 | 8/1969 | Polanyi | 128/2 |
| 3,575,162 | 4/1971 | Gaarder | 128/2.05 T |
| 3,602,213 | 8/1971 | Howell | 128/2.05 F |
| 3,704,706 | 12/1972 | Herczfeld et al. | 128/2 R |
| 3,910,701 | 10/1975 | Henderson et al. | 356/39 |
| 3,980,075 | 9/1976 | Heule | 128/2.05 R |
| 3,993,047 | 11/1976 | Peek | 128/2.05 P |
| 4,029,085 | 6/1977 | DeWitt et al. | 128/2 R |
| 4,249,540 | 2/1981 | Koyama et al. | 128/666 |
| 4,407,290 | 10/1983 | Wilber | 128/633 |
| 4,423,736 | 1/1984 | DeWitt et al. | 128/633 |
| 4,448,534 | 5/1984 | Wertz et al. | 356/435 |
| 4,494,550 | 1/1985 | Blazek et al. | 128/664 |
| 4,510,938 | 4/1985 | Jöbsis et al. | 128/633 |
| 4,652,136 | 3/1987 | Harjunmaa | 356/408 |
| 4,723,554 | 2/1988 | Oman et al. | 128/664 |
| 4,788,982 | 12/1988 | Gedeon et al. | 128/670 |
| 4,797,000 | 1/1989 | Curtis | 356/436 |
| 4,813,000 | 3/1989 | Wyman et al. | 34/526 |
| 4,854,699 | 8/1989 | Edgar, Jr. | 356/41 |
| 4,862,894 | 9/1989 | Fujii | 128/666 |

(List continued on next page.)

OTHER PUBLICATIONS

Affidavit of Frank H. Erdman executed Oct. 13, 1993, together with attached experimental data.

Primary Examiner—Angela D. Sykes
Assistant Examiner—Robert L. Nasser, Jr.
Attorney, Agent, or Firm—Burns, Doane, Swecker & Mathis, L.L.P.

[57] ABSTRACT

A non-invasive method and apparatus for sensing relative blood conditions in extremities, such as using photoelectric dermachromography to measure differential blood flow and/or pooling between extremities, for the purpose of diagnosing cardiovascular conditions. Reflective colorimeters are employed for performing comparative light reflection rheology (LRR). The resting, steady-state LRR for both the left and right palms are simultaneously measured when both arms are in a raised, steady-state condition, and again when both arms are in a lowered, steady-state condition, thereby providing a repeatable measurement of overall vasomotor tone, the tone of the smooth muscles of the arterial walls. Two portable light gauges are used, each including a plurality of light sources such as light-emitting diodes (LEDs) arranged around at least one light detector. Each gauge is removably attachable to the palms of the hands of the patient whose vasomotor tone is to be determined. The gauges are removably attached to the palms so that the hands are movable, and measurements are taken of both hands in a raised, substantially steady-state UP condition, and then again while both hands are in a lowered, substantially steady-state DOWN condition. After a series of these UP and DOWN measurements are taken, the gauges are switched and another series of UP and DOWN measurements with the gauges reversed are taken. Each gauge is independently calibrated by using standardized reference scales.

40 Claims, 17 Drawing Sheets

U.S. PATENT DOCUMENTS

| | | | |
|---|---|---|---|
| 4,865,038 | 9/1989 | Rich et al. | 128/633 |
| 4,907,594 | 3/1990 | Muz | 128/633 |
| 4,927,264 | 5/1990 | Shiga et al. | 356/41 |
| 5,009,231 | 4/1991 | Schmitt et al. | 128/633 |
| 5,054,487 | 10/1991 | Clarke | 128/633 |
| 5,054,488 | 10/1991 | Muz | 128/633 |
| 5,080,098 | 1/1992 | Willett et al. | 128/633 |

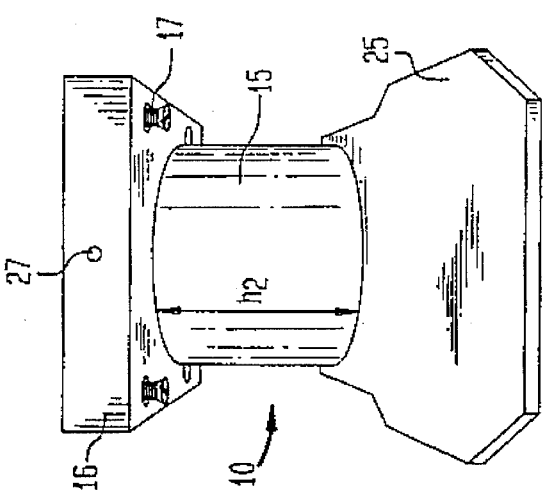
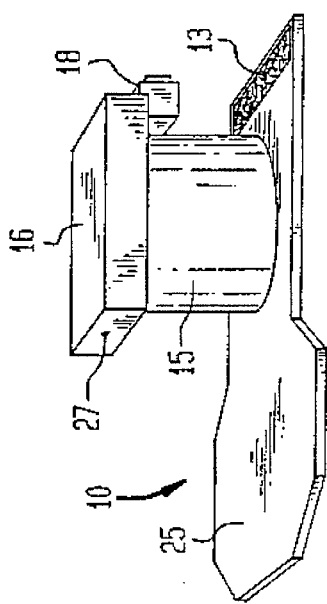
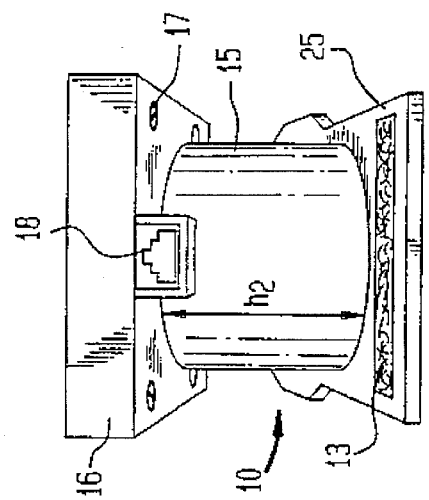

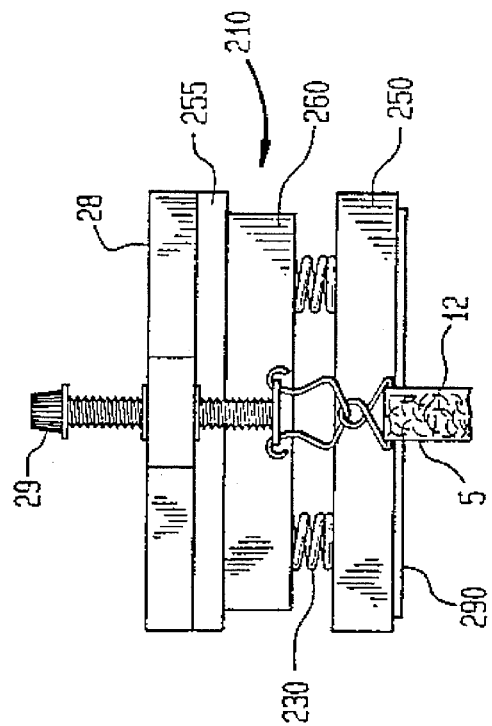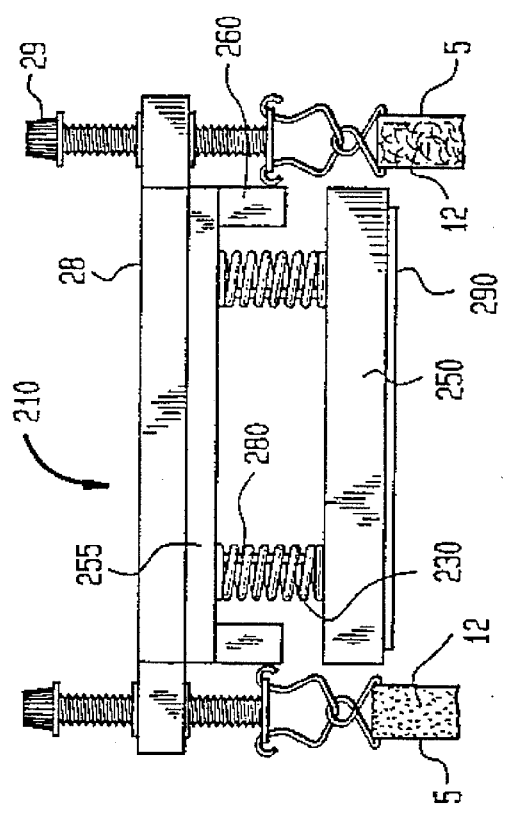

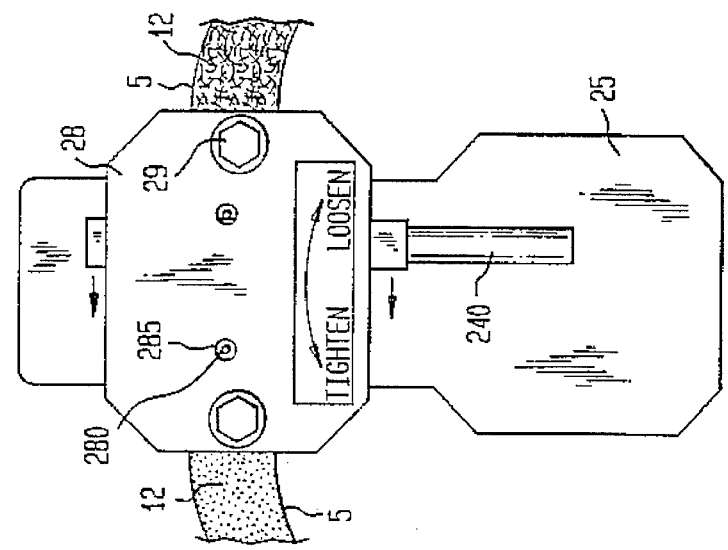
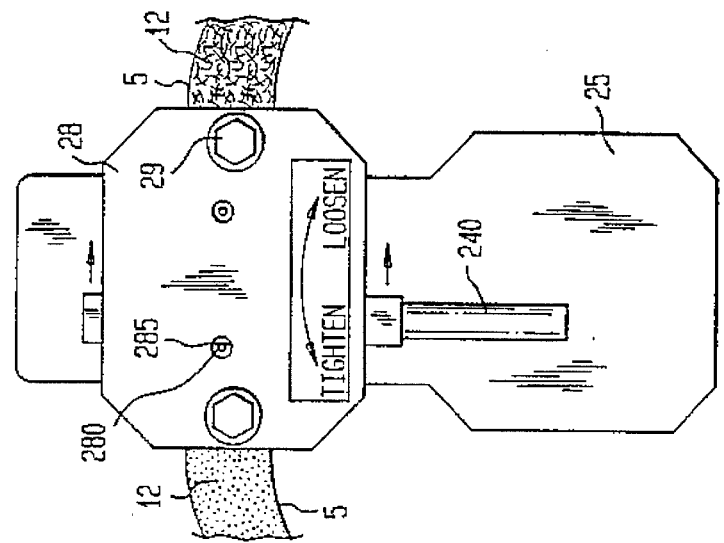
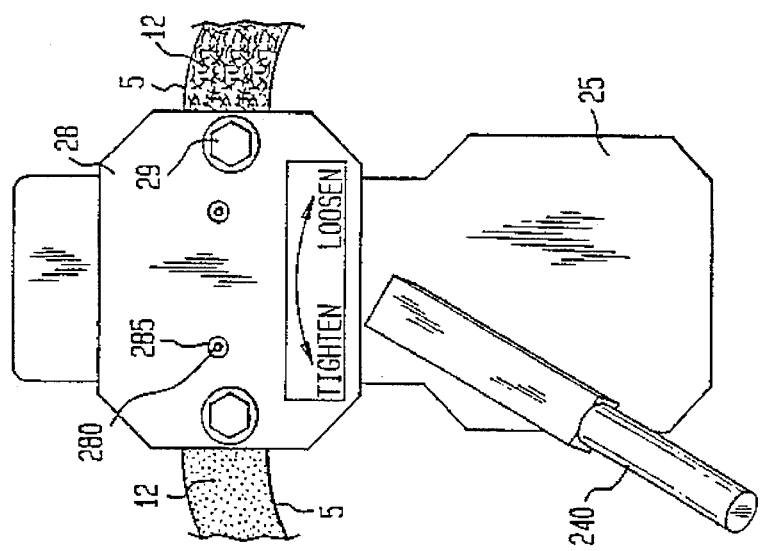

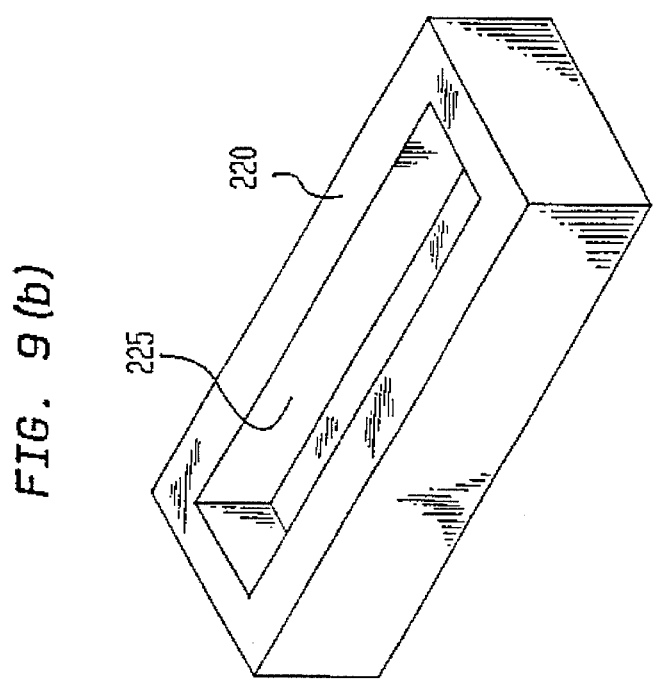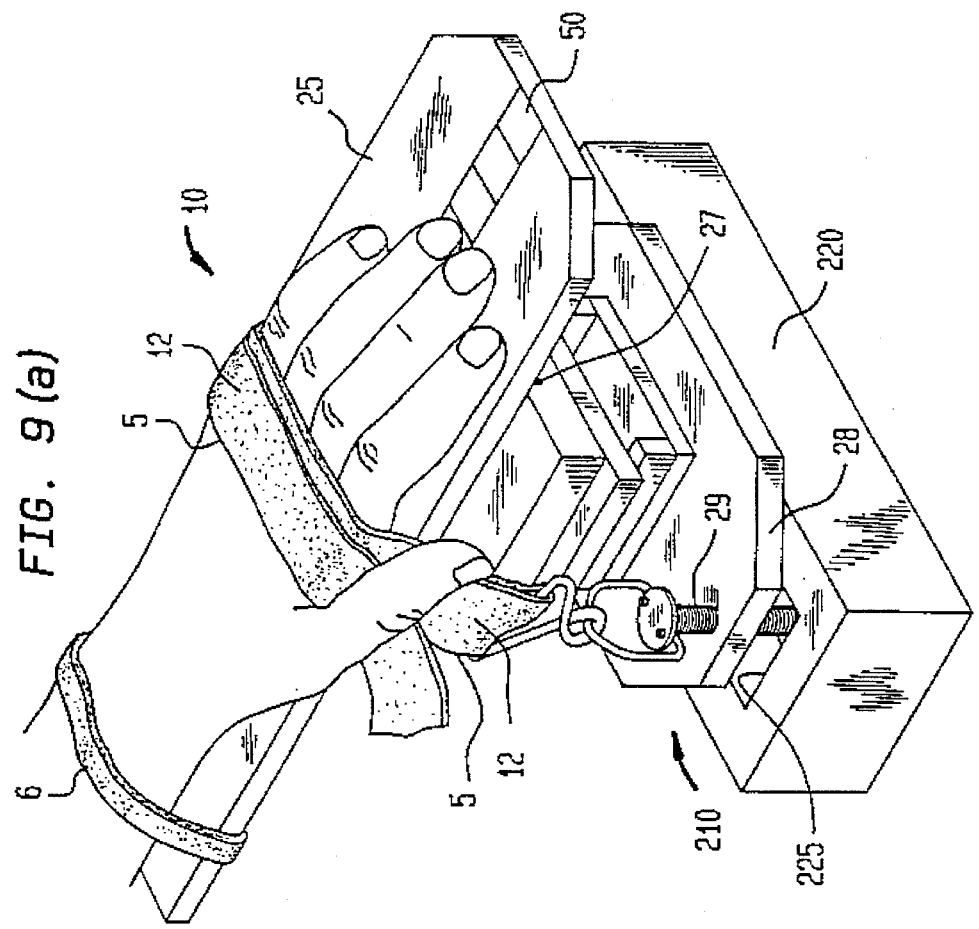

FIG. 14

PATIENT CODE:
TREATMENT: 0-0 MIN
TIME SINCE LAST MEAL: 1:08
OPERATOR NAME:
GAUGE: G-10
VOICE: 62

PATIENT NAME:
TEST NUMBER: 903-1
DATE: 7/5/1992  TIME: 9:38
BAROMETER: 29.82
BLOOD PRESSURE:
RESULT: 1.8750 1.7917 1.9583

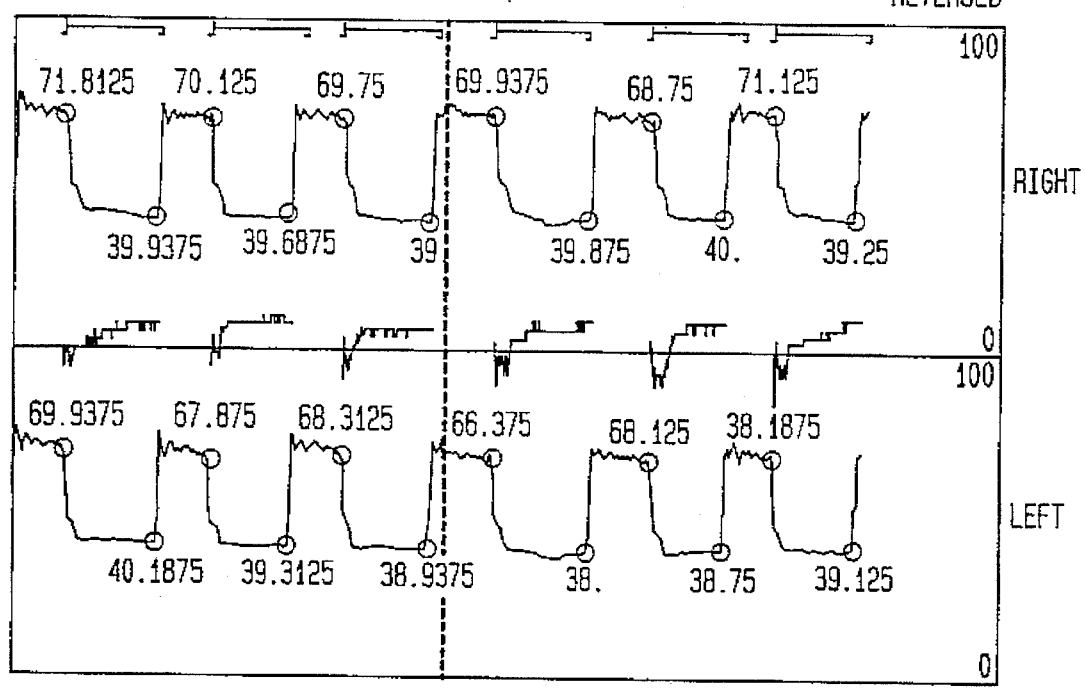

DIFF: 2.13 1.88 1.33 | 1.69 1.38 2.81
DX:    10 24 9    | 12 12 13           AVERAGING WIDTH, SP: 25 EP: 25

|  | NORMAL | REVERSED | AVERAGE | DIFFERENCE |
|---|---|---|---|---|
| RIGHT UP ($R_U$) | 70.5625 | 69.9375 | 70.2500 | 0.6250 |
| RIGHT DOWN ($R_D$) | 39.5417 | 39.7083 | 39.6250 | -0.1667 |
| RIGHT DELTA ($\Delta_R$) | 31.0208 | 30.2292 | 30.6250 | 0.7917 |
| LEFT UP ($L_U$) | 68.7083 | 66.8958 | 67.8021 | 1.8125 |
| LEFT DOWN ($L_D$) | 39.4792 | 38.6250 | 39.0521 | 0.8542 |
| LEFT DELTA ($\Delta_L$) | 29.2292 | 28.2708 | 28.7500 | 0.9583 |
| R - L DELTA ($\Delta_{R-L}$) | 1.7917 | 1.9583 | 1.8750 | -0.1667 |
| AVG UP ($R_U+L_U$)/2 | 69.6354 | 68.4167 | 69.0260 | 1.2188 |
| AVG. DOWN ($R_D+L_D$)/2 | 39.5104 | 39.1667 | 39.3385 | 0.3438 |
| AVG DELTA ($\Delta_R+\Delta_L$)/2 | 30.1250 | 29.2500 | 29.6875 | 0.8750 |
| DX | 14.3333 | 12.3333 | 13.3333 | 2.0000 |

MEMO:
  CAL 0/0 BAIN -1/+1, REV. 0/0 GAIN 0/-1, GAUGES AT 135mm,

FIG. 15

PATIENT CODE:  
TREATMENT: 0-0 MIN  
TIME SINCE LAST MEAL: 1:08  
OPERATOR NAME:  
GAUGE: G-10  
VOICE: 62

PATIENT NAME:  
TEST NUMBER: 903-2  
DATE: 7/5/1992  TIME: 9:38  
BAROMETER: 29.82  
BLOOD PRESSURE:  
RESULT: 0.5208 -0.1667 1.2083

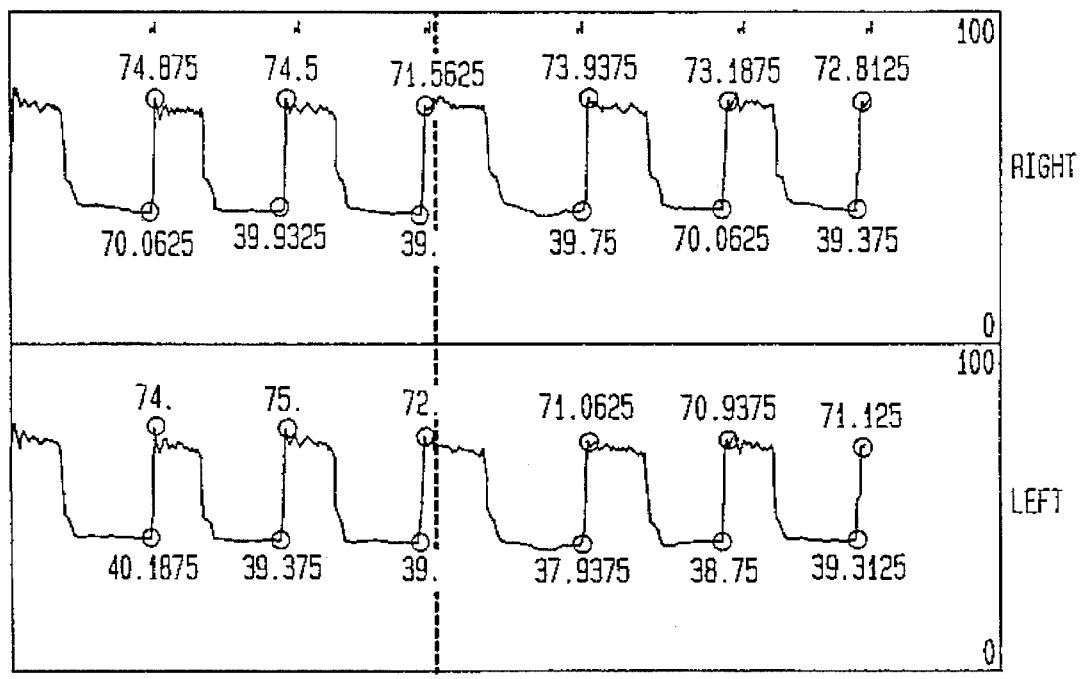

DIFF: 1.00 -1.06 -0.44 | 1.06 0.94 1.63  
DX: 24 1 12 | 25 25 28               AVERAGING WIDTH, SP: 1 EP: 1

|  | NORMAL | REVERSED | AVERAGE | DIFFERENCE |
|---|---|---|---|---|
| RIGHT UP ($R_U$) | 73.6458 | 73.3125 | 73.4792 | 0.3333 |
| RIGHT DOWN ($R_D$) | 39.6667 | 39.7292 | 39.6979 | -0.0625 |
| RIGHT DELTA ($\Delta_R$) | 33.9792 | 33.5833 | 33.7812 | 0.3958 |
| | | | | |
| LEFT UP ($L_U$) | 73.6667 | 71.0417 | 72.3542 | 2.6250 |
| LEFT DOWN ($L_D$) | 39.5208 | 38.6250 | 39.0937 | 0.8542 |
| LEFT DELTA ($\Delta_L$) | 34.1458 | 32.3750 | 33.2604 | 1.7708 |
| | | | | |
| R - L DELTA ($\Delta_{R-L}$) | -0.1667 | 1.2083 | 0.5208 | -1.3750 |
| | | | | |
| AVG UP ($R_U+L_U$)/2 | 73.6563 | 72.1771 | 72.9167 | 1.4792 |
| AVG. DOWN ($R_D+L_D$)/2 | 39.5937 | 39.1973 | 39.3958 | 0.3958 |
| AVG DELTA ($\Delta_R+\Delta_L$)/2 | 34.0625 | 32.9792 | 33.5208 | 1.0833 |
| | | | | |
| DX | 12.3333 | 26.0000 | 19.1667 | -13.6667 |

MEMO:  
CAL 0/0 BAIN -1/+1, REV. 0/0 GAIN 0/-1, GAUGES AT 135mm,

METHOD AND APPARATUS FOR CARDIOVASCULAR DIAGNOSIS

The present application is a continuation-in-part of U.S. patent application Ser. No. 07/922,780 filed Jul. 31, 1992, now U.S. Pat. No. 5,365,924, herein incorporated by reference.

BACKGROUND OF THE INVENTION

1. Field of the Invention

The present invention relates to a non-invasive method and apparatus for diagnosing cardiovascular conditions. In particular, the present invention relates to use of a pair of colorimeters to perform non-invasive comparative light reflection rheology on the palms of the hands.

2. Background Art

According to the Erdman Therapy developed around 80 years ago by Frederick Erdman, there are two broad classes of circulatory types: (1) those who react to stress, disease, trauma, and irritant substances by lowering the arterial tone, the tone of the smooth muscles of the arterial walls, and (2) those of a much larger class (probably 90–95% of the population) who react by increasing arterial tone, also known as vasomotor tone.

For example, a very stressful situation may cause some individuals to feel faint while others become agitated. The reactions are neurologically mediated and result in the first instance (faintness) in profound vessel dilation, and, in the second instance (agitation) in vessel constriction. The medical treatments appropriate for anxiety-induced faintness as opposed to anxiety-induced agitation are quite different.

Patients who have low vasomotor tone live to some degree in a perpetual faint, which they may or may not perceive, and these patients are likely to fare poorly on conventional medical therapies because these conventional therapies inadvertently may have vasodilating effects. One of the reasons this class of patients is overlooked is that they comprise only a small minority of the population.

A fundamental objective of the Erdman Therapy is to improve the rate of blood flow for both classes of circulatory types. The majority of people, who fall into the "normal" circulatory class in which their arteries become too constricted because the tone of the smooth muscles of their arterial walls is excessive, find that their condition may be relieved through the use of heat, massage, and ultrasound therapies. All of these procedures and many medicines tend to reduce arterial tone, thereby improving the rate of blood flow in the majority of people.

Frederick Erdman's primary contribution was recognizing that the remaining minority of the population fall into a circulatory condition where at least some of their arteries are too dilated because their vasomotor tone is below normal. In this case, the indicated treatment is exactly opposite to that for the former group: namely, cold applications are required on the spinal muscles or at least portions thereof.

The most frequent medical syndrome in which low vasomotor tone is a major component is orthostatic hypotension associated with sensitivity to heat and fatigue from prolonged standing. Multiple sclerosis, severe chronic headache syndromes including migraines, insulin-dependent diabetes, hypoglycemia, hay fever or other allergies, and hyperactivity in children are all associated with this low vasomotor tone condition. Many juvenile asthmatics are also in this category.

Even though the great majority of the population fall into the first group which benefit from heat and massage and ultrasound treatments applied to the back, Erdman Therapy is uniquely capable of benefitting patients who are initially in the second group and require cold on the spine. By following a carefully monitored program of cold applications, patients can be transformed from the second group requiring cold applications to a group having the normal circulatory condition. Alternatively, those who are initially in the first group follow a program of gentle massage and warming type treatment applied to the back muscles to reduce excessive arterial tone.

By recognizing the existence of these two diametrically opposed groups and applying appropriate treatment to each, the circulation and blood pressure of both groups can be improved.

Traditionally, under the Erdman Therapy, highly trained professionals perform manual palpitation of the radial pulses to evaluate vasomotor tone, manually sensing the shape and amplitude of the pulse, a procedure devised to determine how to categorize a patient. The Yellow Emperor of China emphasized the importance of the radial pulse in his medical treatise of circa 2700 B.C., but Western medicine has not given much attention to pulse analysis, even though occasionally physicians have casually observed that the two radial pulses of an individual can often be quite different. Usually it is assumed that this condition of differing radial pulses is an anatomical variation rather than a variable physiological condition. While the radial pulses are both physiologically under the control of the central nervous system, they are, in particular, supplied by different sets of paraspinal ganglia. It appears that the afferent fibers supplying those ganglia for the right and left limbs do not symmetrically arise from the same sites, especially within the splanchnic (visceral) circulation. This is important because it may explain why patients with low vasomotor tone have gastrointestinal symptoms, as well as peripheral symptoms, and that both types of symptoms resolve when proper tone is restored.

The hallmark of patients who suffer from low vasomotor tone is a strong left pulse, especially after a gentle challenge of the appropriate spinal nerves with cooling. Pulse strength is characterized by pulse volume, pulse amplitude, and perceptible "push-through". Persons with low vasomotor tone can be treated by gentle intermittent applications of a cooling agent on the paraspinal nerve reflexes until the right pulse becomes dominant and both pulses have improved in tone. By carrying out the indicated therapies to correct each type of imbalance, a patient's circulatory condition can be restored to an optimum condition and symptoms can be reduced or alleviated, often dramatically.

Previous attempts to develop a method and apparatus to categorize non-invasively the vasomotor tone of patients without using manual palpitation of the radial pulses have not been successful. In the past, electromechanical radial pulse detectors have not proven to be adequately accurate and are not sensitive enough. Blood flowmeter measurements made with various types of plethysmographs, ultrasound devices, electromagnetic devices, and nuclear magnetic resonance (NMR) flow imaging techniques have all been ineffective.

The present invention includes a means for determining the type of therapy (cold or warm treatments) which a patient requires. It is based on a technique for measuring differential blood accumulation between the left and right arms.

After thousands of tests, the difference in blood pooling has been shown to be an extremely accurate method (over 99%) of qualitatively showing the vasomotor tone (i.e., high verses low tone) of the vascular system.

Non-invasive monitoring of physiological conditions, particularly cardiovascular conditions, is known.

For example, U.S. Pat. No. 3,602,213 to Howell et al. discloses an apparatus and method for photoelectric dermachromography, employed for indicating the flow of blood in the capillary or arterial bed of the skin, and also for producing fine-grained examinations of the pulsations of the blood in the arterial and capillary systems. The Howell et al. apparatus graphically indicates and records, by electronic means, the differential blood flow to the skin in various related body areas. When such differential blood flow exists, this fact indicates to the examining physician or technician that one or more obstructions are present in the arterial system, and the location of such obstructions is determinable from the position at which the apparatus is applied to the skin of the patient and by isolation of arterial branches by manual occlusion of adjacent branches by pressure. The Howell et al. instrumentation and methods by which the relative blood flow to different areas of the skin may be detected and then visibly indicated and recorded do not require the exercise of any unusual skills, substantially eliminating the human error element in using the apparatus so that, with practice, a technician may use the apparatus satisfactorily without requiring the services of a physician. In particular, the Howell et al. patent discloses a method and apparatus for detecting occlusions in one of the internal carotid arteries by the differential sensing of epidermal blood flow in the supraorbital areas. A pair of photoelectric transducers that sense the relative absorption or reflection of light by the blood at the surface of the skin as an indication of blood flow are positioned over the supraorbital notches above the eyes. The sensor outputs are compared, and any unbalance indicates an occlusion in one of the carotid arteries.

U.S. Pat. No. 4,494,550 to Blazek et al. discloses quantitative evaluation of peripheral venous drainage disorders and arterial blood flow disorders in man, objectively detecting changes in cutaneous circulation under physical strain, and detecting obstacles to venous flow in the extremities. A plurality of radiation sources are directed onto the skin of the area of the respective extremity, and a radiation receiver measures the amount of radiation reflected or dispersed back by the cutaneous vascular plexus, and a temperature sensor simultaneously measures the skin temperature. An electronic evaluation circuit detects and records the progress of the reflected or dispersed amount of radiation and the skin temperature as a function of time. The simultaneous attachment of two or more Blazek et al. measuring heads to the electronic evaluation circuitry of the measuring apparatus enables the determination of the differences in measured values between normally supplied and poorly supplied areas of the skin.

U.S. Pat. No. 4,788,982 to Gedeon et al. discloses a device for determining the depth of anaesthesia of a patient including optical measuring means for measuring on a part of the patient an optical parameter such as the light reflected from this part of the patient. The light reflection is influenced by the circulation of the blood through this part of the patient's body, and produces an electric signal varying in accordance with this optical parameter. This signal is related to the periodic variations in the blood pressure of the patient with a frequency coinciding with the patient's heart frequency. The degree of anaesthesia of the patient can be correlated with the blood pressure variations and heart frequency extracted from the electric signal.

Both the Howell et al. and the Blazek et al. patents disclose differential sensing of blood flow using a pair of transducers that sense the relative absorption or reflection of light by epidermal blood in the respective body areas. However, both the Howell et al. and the Blazek et al. transducers disclose exposing relatively small areas of skin to the light, whereas the need exists for a device that exposes much larger areas of skin (for example, the skin of the palms) to the light. The Blazek et al. transducers preferably are also equipped with lenses giving a small aperture so that the emitted selective optical radiation can penetrate deep into the skin. The need exists, however, for a device that does not necessarily require the light transducers to be equipped with lenses.

Furthermore, as applied to the differential sensing of blood flow to the supraorbital areas, the Howell et al. patent requires that enough pressure is applied to the areas measured to eliminate the blood contributions to these areas from the superficial temporal, angular, and occipital arteries, leaving the internal carotid arteries as the only suppliers. The need exists, however, for a device that determines overall vasomotor tone without requiring the application of any such compression since the total blood flow to each hand is one object of the measurements using such a vasomotor tone sensor, not the detection of the individual contributions of particular arteries.

The Blazek et al. patent requires each transducer also to measure the temperature of the respective body area, and the plurality of sources of radiation are required to effect homogeneous cutaneous transillumination without subjecting the skin to elevated temperatures. The need exists, however, for a vasomotor tone sensor that does not require measurement of the temperature of the illuminated body area, and does not place any restrictions on subjecting the skin to elevated temperatures, other than the restriction of not raising the temperatures beyond what would be comfortable to the patient.

Furthermore, the Howell et al. patent discloses differential sensing of blood flow in the respective body areas using a pair of transducers so that any unbalance in the comparison of sensor output indicates an occlusion in one of the blood-supplying vessels, resulting perhaps from partial obstruction due to arteriosclerosis or thrombophlebitis. However, the Howell et al. apparatus and method for detecting such static and non-varying occlusions are unable to detect and repeatably indicate dynamic and variable physiological conditions such as overall vasomotor tone.

The Blazek et al. patent discloses recording the results of the light reflection rheology (LRR) procedure both before and after a change in the patient's physical position. In particular, the LRR curve is recorded when the measuring head is affixed to the inner side of the relaxed leg with the patient sitting with legs pendant. Then, the patient carries out a movement program, such as dorsal flexion of the ankle not more than 10 times in 15 seconds followed by letting the leg hang again in a relaxed resting state, causing the cutaneous vessels to empty, leading to changes in the cutaneous reflection that are also recorded. The need exists, however, for a vasomotor sensor that is not dependent on any transient emptying and/or refilling of the blood vessels. For example, a vasomotor sensor that measures the resting, steady-state LRR for both the left and right palms simultaneously when both arms are in a raised UP condition and again when both arms are in a lowered DOWN condition, would provide a better and more repeatable measurement of overall vasomotor tone.

The Gedeon et al. patent is representative of non-invasive LRR devices that can be used to monitor an overall passive and static physiological condition, for example, the degree or depth of anaesthesia of a patient. The need exists, on the other hand, for a method and apparatus that enables the use of non-invasive comparative LRR devices to monitor continuously an overall active and variable physiological condition, for example, the vasomotor tone of a patient. Further, it would be most desirable for such a vasomotor sensor to be portable, light-weight, relatively inexpensive, and easy to use.

SUMMARY OF THE INVENTION

The present invention provides a non-invasive method and apparatus for sensing relative blood conditions (blood flow and/or blood pooling) in extremities, such as using photoelectric dermachromography and skin colorimetry to measure relative blood condition differences between extremities, for the purpose of diagnosing cardiovascular conditions. In particular, the present invention provides reflective colorimeters to perform comparative light reflection rheology (LRR) on the extremities. The present invention measures the resting, steady-state LRR for both the left and right palms simultaneously when both arms are in a raised UP condition, and again when both arms are in a lowered DOWN condition, thereby providing a repeatable measurement of circulatory conditions.

Preferred embodiments of the present invention use two portable, light-weight, relatively inexpensive light gauges, each including a plurality of light sources such as light-emitting diodes (LEDs) symmetrically arranged around at least one light detector. Alternative to the plurality of LEDs, the light source can be a remotely located incandescent light connected to both light gauges by fiber optics, the optical fibers receiving light from the incandescent light at one end and forming a ring around the light detector in the light gauges at the other end. Similarly, fiber optics can be used to remotely locate at least one light detector from the light gauges.

Each gauge is easily attachable to the palms of the hands of the patient whose vasomotor tone is to be determined and categorized.

The gauges are attached to the palms so that the hands are independently movable, and measurements are taken while the left and right hands are simultaneously in a raised, substantially steady-state UP condition, and then again while the left and right hands are simultaneously in a lowered, substantially steady-state DOWN condition. After a series of these UP and DOWN measurements are taken, the gauges are switched relative to which hand they are placed on and another series of UP and DOWN measurements with the reversed gauges are taken. For example, three sets of UP and DOWN measurements are taken in the first or normal attachment, and three sets of UP and DOWN measurements are taken in the second or reversed attachment.

Each gauge is independently calibrated by using preheated, standardized light gray and dark gray or red scales.

BRIEF DESCRIPTION OF THE DRAWINGS

The foregoing and other features of the present invention will become apparent to people skilled in the art to which the invention pertains from the following detailed description when read in conjunction with the drawings, in which:

FIGS. 3(a), 3(b), and 3(c) are front, side, and back views, respectively, of the light gauge of FIG. 1;

FIGS. 6(a) and 6(b) are front and side views, respectively, of the spring attachment assembly of FIG. 1;

FIGS. 8(a), 8(b), and 8(c) are top views of the light gauge and spring attachment assembly of FIG. 1 with a spacer block in various configurations;

FIGS. 9(a) and 9(b) are perspective views of support blocks useful for implementing an embodiment of the present invention;

FIG. 14 is representative of a print-out after a run on a patient with critical points marked for a "filling" measurement;

FIG. 15 is representative of a print-out after a run on a patient with critical points marked for a "dumping" measurement;

DESCRIPTION OF THE PREFERRED EMBODIMENTS

Figure 1:
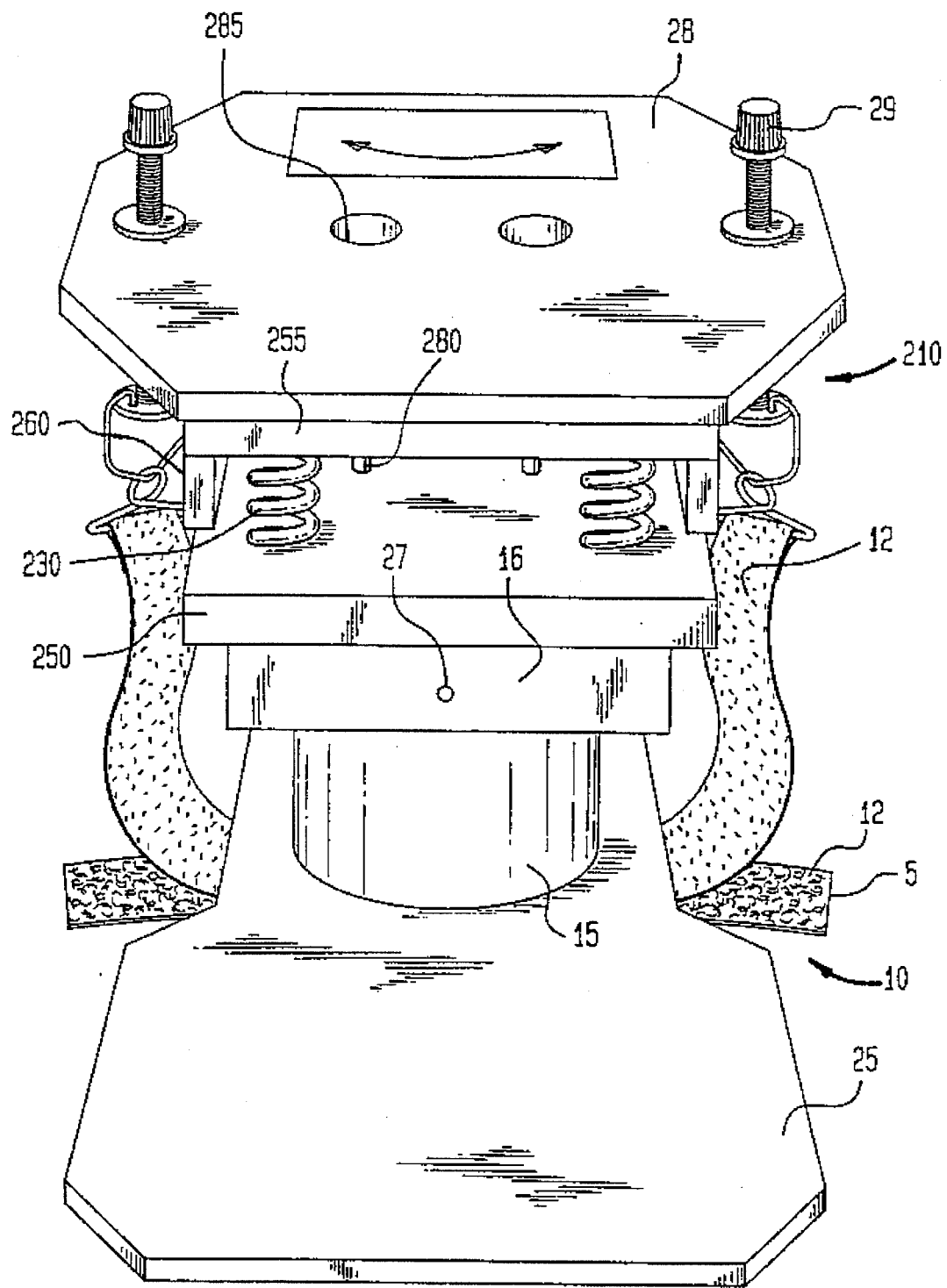
FIG. 1 is a perspective view of a light gauge and spring attachment assembly according to a first embodiment of the present invention.
Figure 2B:
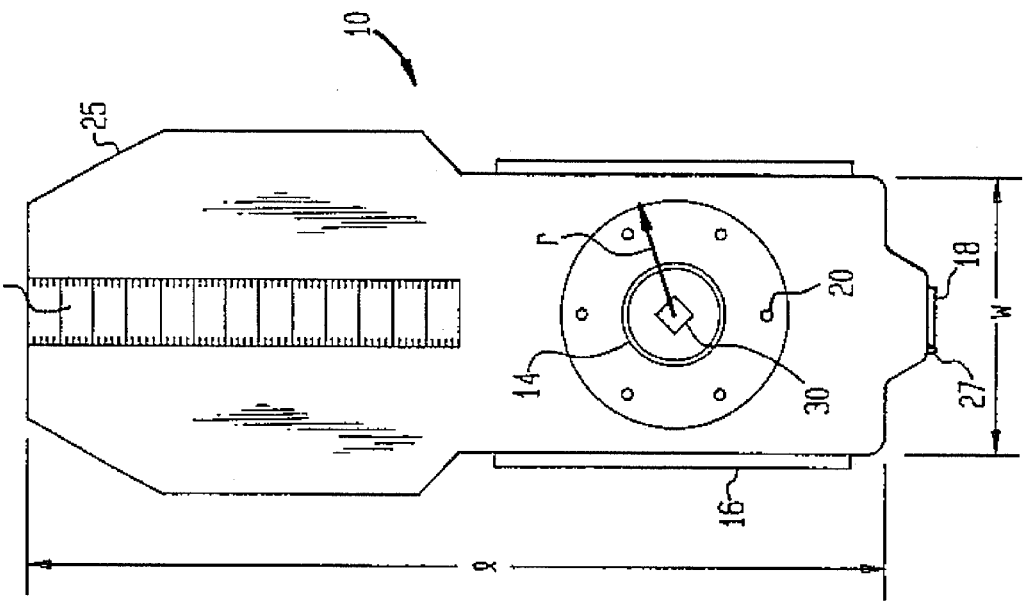
FIGS. 2(a) and 2(b) are top and bottom views, respectively, of the light gauge of FIG. 1.

A light gauge 10 and spring attachment assembly 210 according to a first embodiment of the present invention are shown in FIG. 1. A substantially opaque black plastic cylinder 15 of height $h_2$ of about 3.5 to 5.0 centimeters, shown in FIGS. 3(a) and 3(c), and inner diameter 2r of about 5.2 centimeters, shown in FIG. 2(b), is disposed on a substantially flat opaque black plastic blade 25, preferably of length l of about 22 centimeters and small width w of about 7.5 centimeters, shown in FIG. 2(b). As an alternative to the opaque black plastic, aluminum can be used to provide better shielding for the elimination of static signals due to the movement of a patient's feet or other causes.

Figure 4:
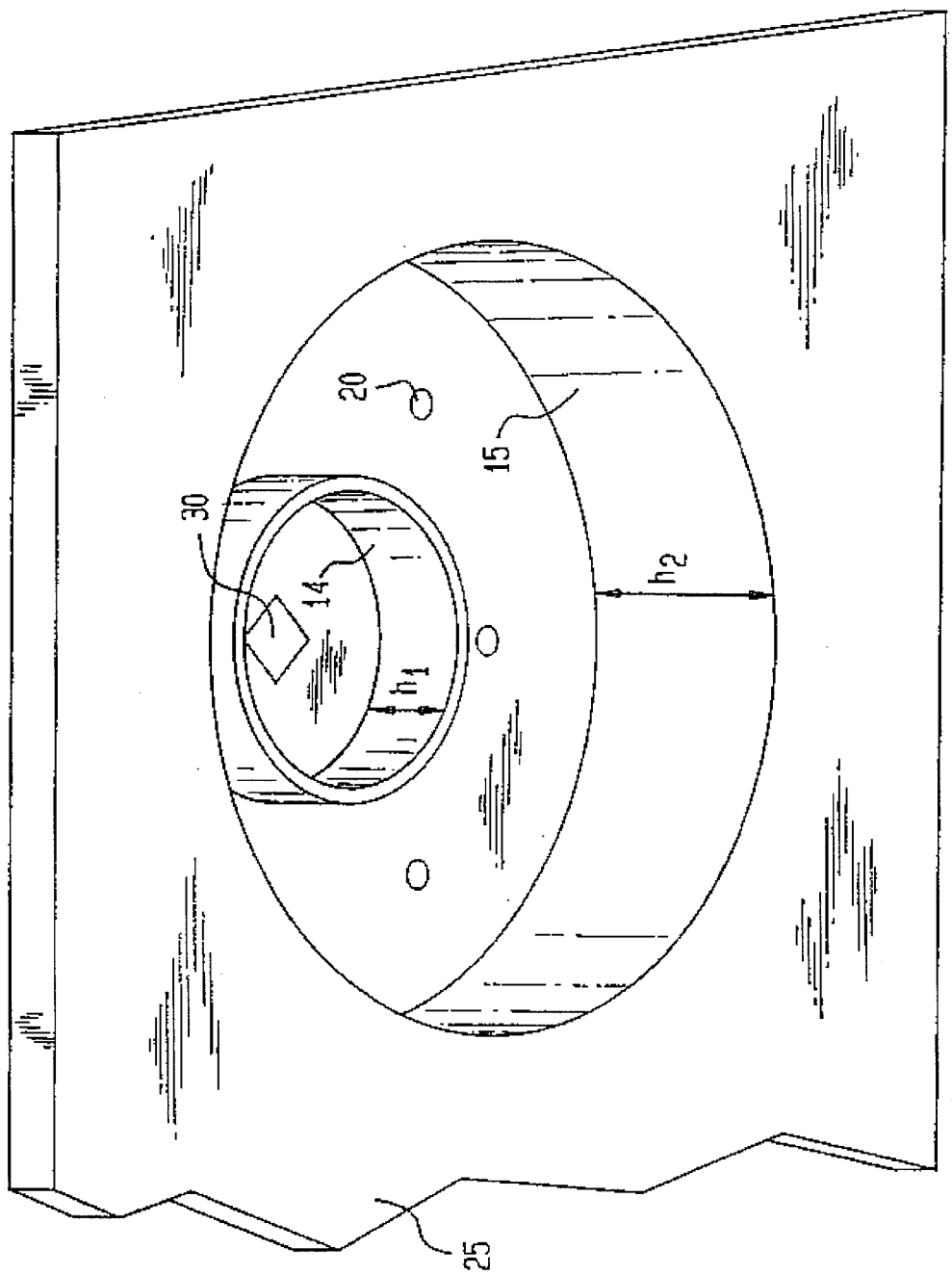
FIG. 4 is a perspective view of a portion of the bottom of the light gauge of FIG. 1.

Six green light-emitting diodes (LEDs) 20, which may be model HLMP-1640 LEDs available from Hewlett-Packard, Inc., or the like, are symmetrically arranged around a photodiode light detector 30, which may be a model S1227-66BR detector available from Hamamatsu, or the like, at one end of cylinder 15 exposed on the underside of blade 25, as shown in FIG. 2(*b*) and in FIG. 4.

Figure 16:
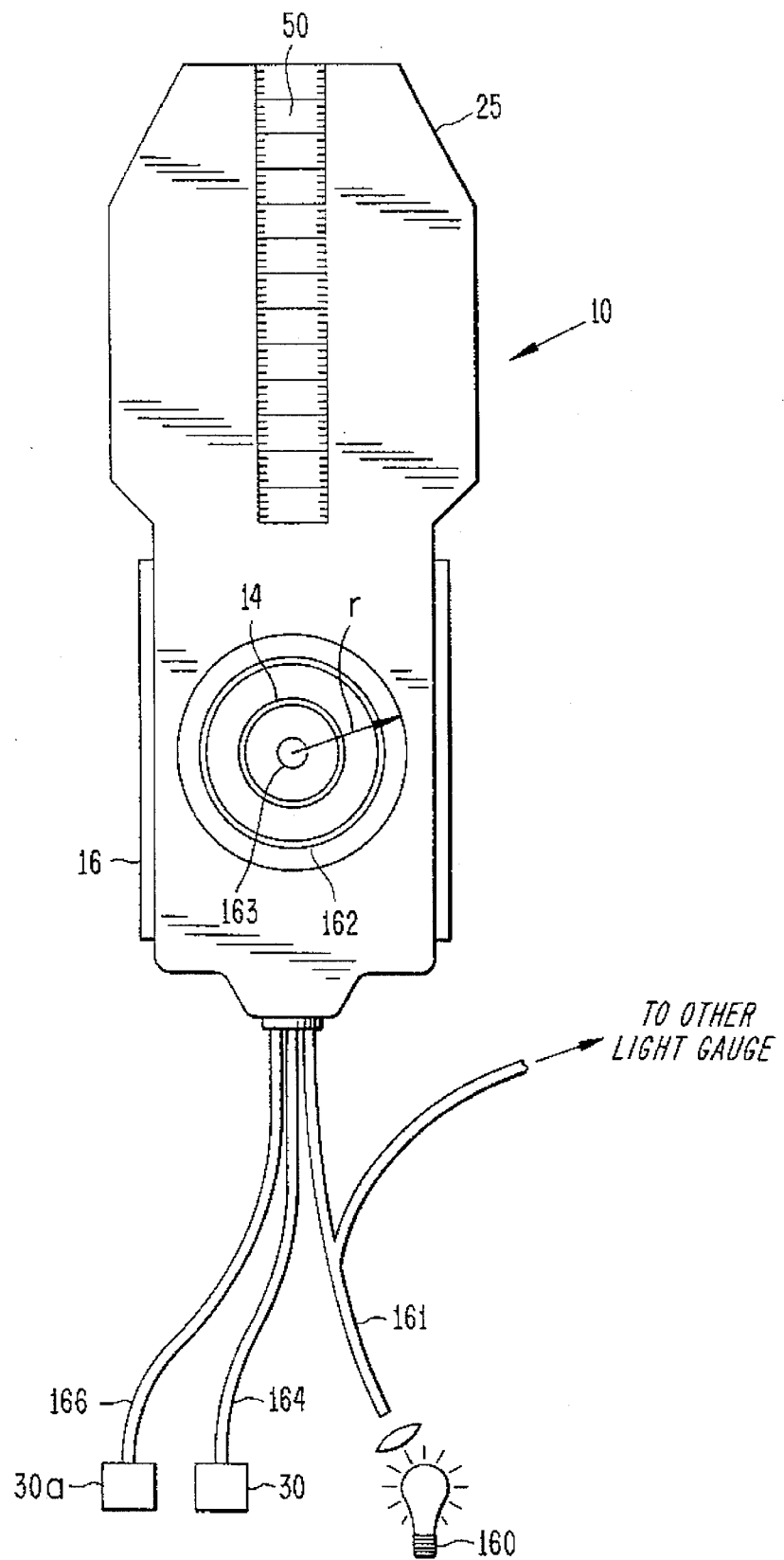
FIG. 16 is a bottom view of a light gauge in accordance with a second embodiment of the present invention.

As an alternative to the six LEDs 20, illumination may be provided by a single remote high intensity incandescent light 160 or the like such as shown in FIG. 16. A fiber optic bundle 161 is connected to the light source 160, the bundle then being divided to supply illumination for each gauge 15. This arrangement ensures that any fluctuation in the light source intensity influences both gauges identically. Also, this configuration permits a circular or ring shaped arrangement 162 of the illumination supply optical fibers surrounding a light receiving center section 163, thereby providing more even illumination.

In the embodiment shown in FIG. 16, the reflected light is picked up at the center of each gauge and conducted through fiber optic bundles 164 to remotely located photodiode light detector or detectors 30, which may be located adjacent or within a controller 70. Removing the detectors 30 and their associated circuitry from the light gauge 10 can reduce calibration drift caused by the heat transferred from the patient's hands (and/or the LEDs 20 in the embodiment of FIG. 17, discussed below) during prolonged use. Also, it is conceivable that only one detector 30 is used on a time share or multiplexed basis, thereby further reducing calibration problems due to component variations.

A feedback optical fiber (or fiber optic bundle) 166 is used to monitor the intensity of the supply light by forming a feedback loop with a feedback light detector 30*a*, such as a photodiode. The feedback light detector 30*a* may be located adjacent or within a controller 70. Alternatively, a feedback light detector 30*a* can be placed in each of the light gauges 10 and the optical fiber 166 eliminated. The feedback loop continuously monitors the light intensity and continuously adjusts the output of the incandescent lamp by controlling the power supply via a conventional comparator circuit, for example, so that fluctuations in the illumination light are reduced or practically eliminated, whether these fluctuations are due to variations in the line voltage supplying the incandescent lamp, or otherwise.

The embodiment shown in FIG. 16 is designed to offer several improvements such as maintaining uniformity of the light source and reducing calibration drift. However, the fiber optic bundles can prove bulky and add additional expense.

Figure 17:
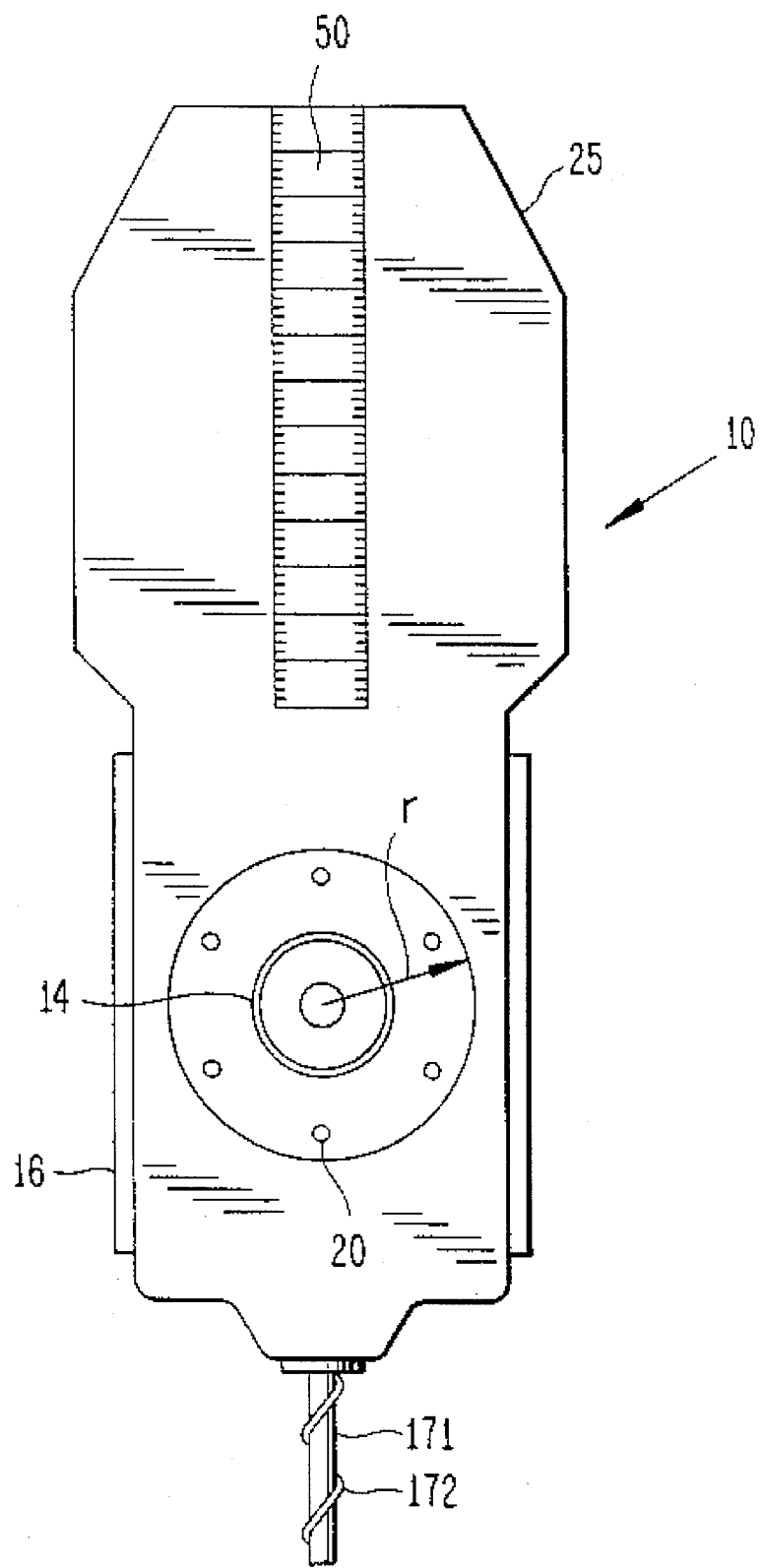
FIG. 17 is a bottom view of a third embodiment of the present invention.

In light of these factors, the embodiment shown in FIG. 17 is another alternative embodiment wherein the light sources are individual photodiodes 20 mounted in the light gauges 10, as in the first embodiment, but a optical fiber (or fiber optic bundle) 171 is used to carry reflected signals from each light gauge 10 to individual photodiode detectors 30 located adjacent or within a controller 70. The diode power leads 172 may be located within or on the fiber optic bundle for convenience.

For simplicity, the first embodiment will be described with respect to the operation of the overall system and other components, as well as describing the method of the present invention. This explanation of the invention is readily adaptable to the second and third embodiments of FIGS. 16 and 17 to persons skilled in the art.

Figure 10:
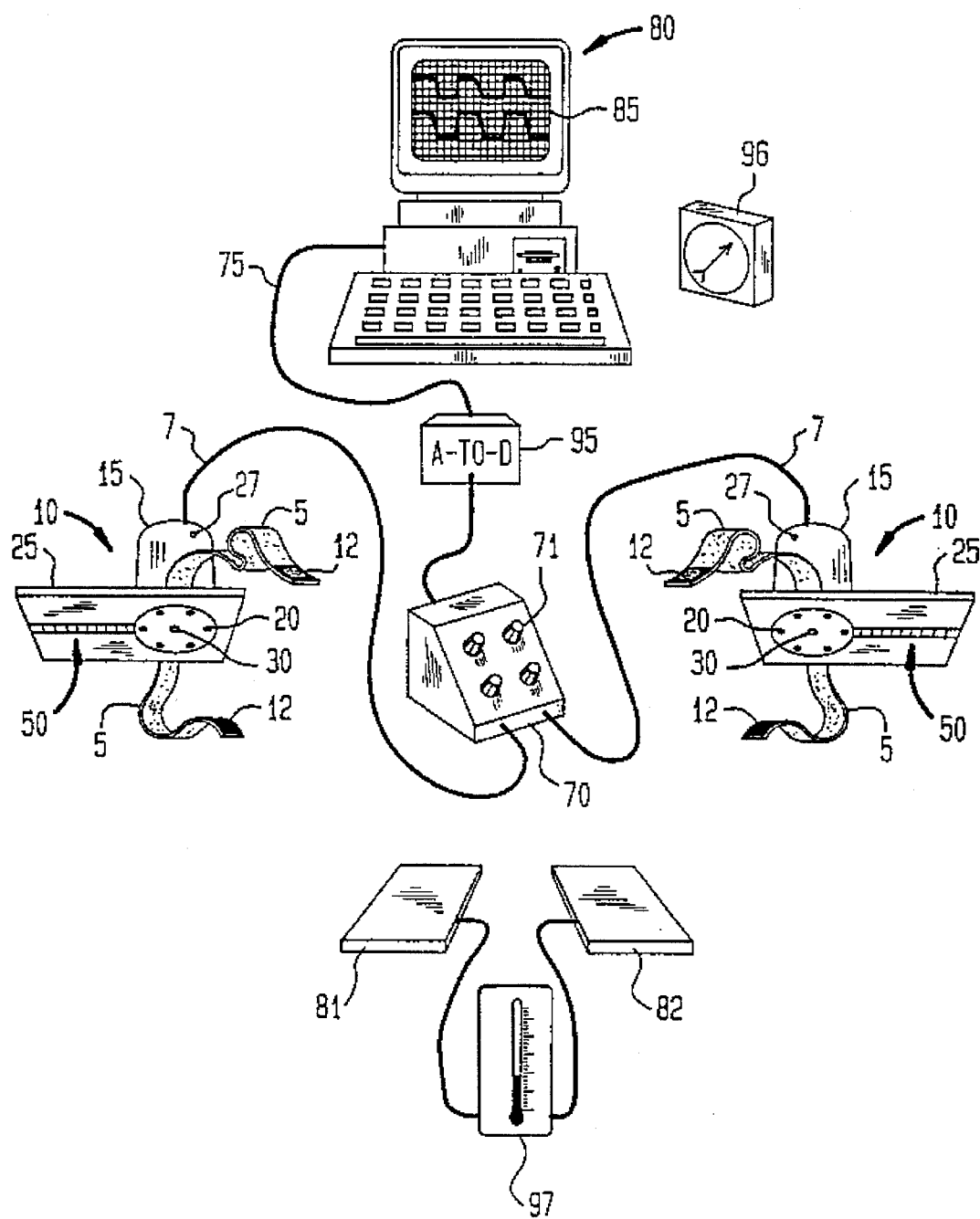
FIG. 10 is a perspective schematic view of a system useful for determining vasomotor tone according to an embodiment of the present invention.
Figure 11:
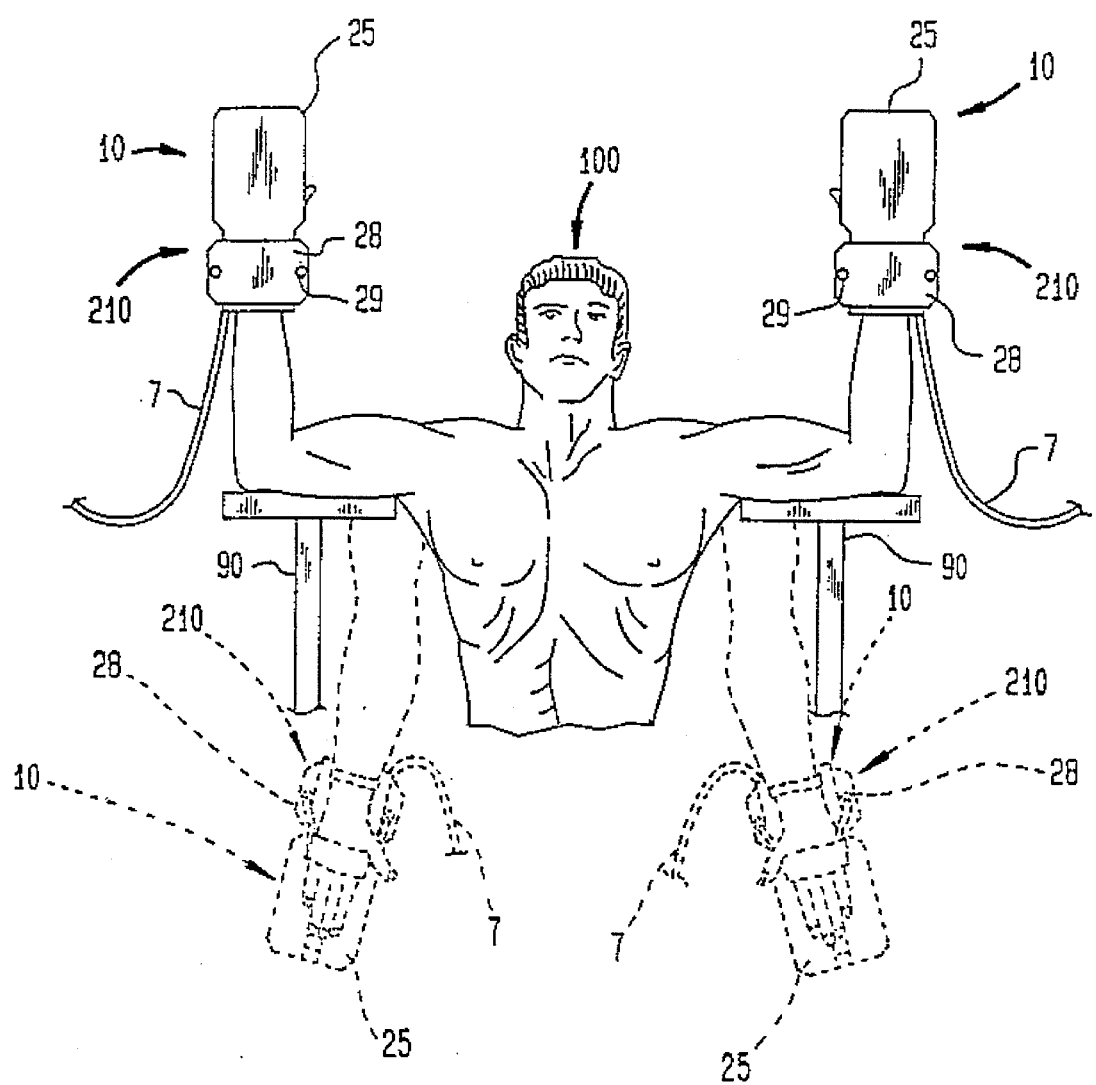
FIG. 11 is a perspective view of an embodiment of the present invention in operation with a human patient.

When energized by control cable 7, shown in FIGS. 10, 11, and 12, connected to light gauge 10 through connector 18, green LEDs 20 illuminate the palm of a hand that is attached to the underside of blade 25 by straps 5 using rubber-backed "Velcro" hook and loop fasteners 12. The connectors 18 are illustrated to be of the type commonly used for telephone jacks. However, in-line, quick disconnect connectors can be used in their place. The relatively large area of the palm illuminated (about 5.2 centimeters in diameter) allows good repeatability and reproducibility in taking measurements from hand to hand, thereby reducing the extreme sensitivity and variability shown, for example, by strain gauges and the above-mentioned Howell et al. and Blazek et al. transducers that are only exposed to a small surface area.

Figure 5:
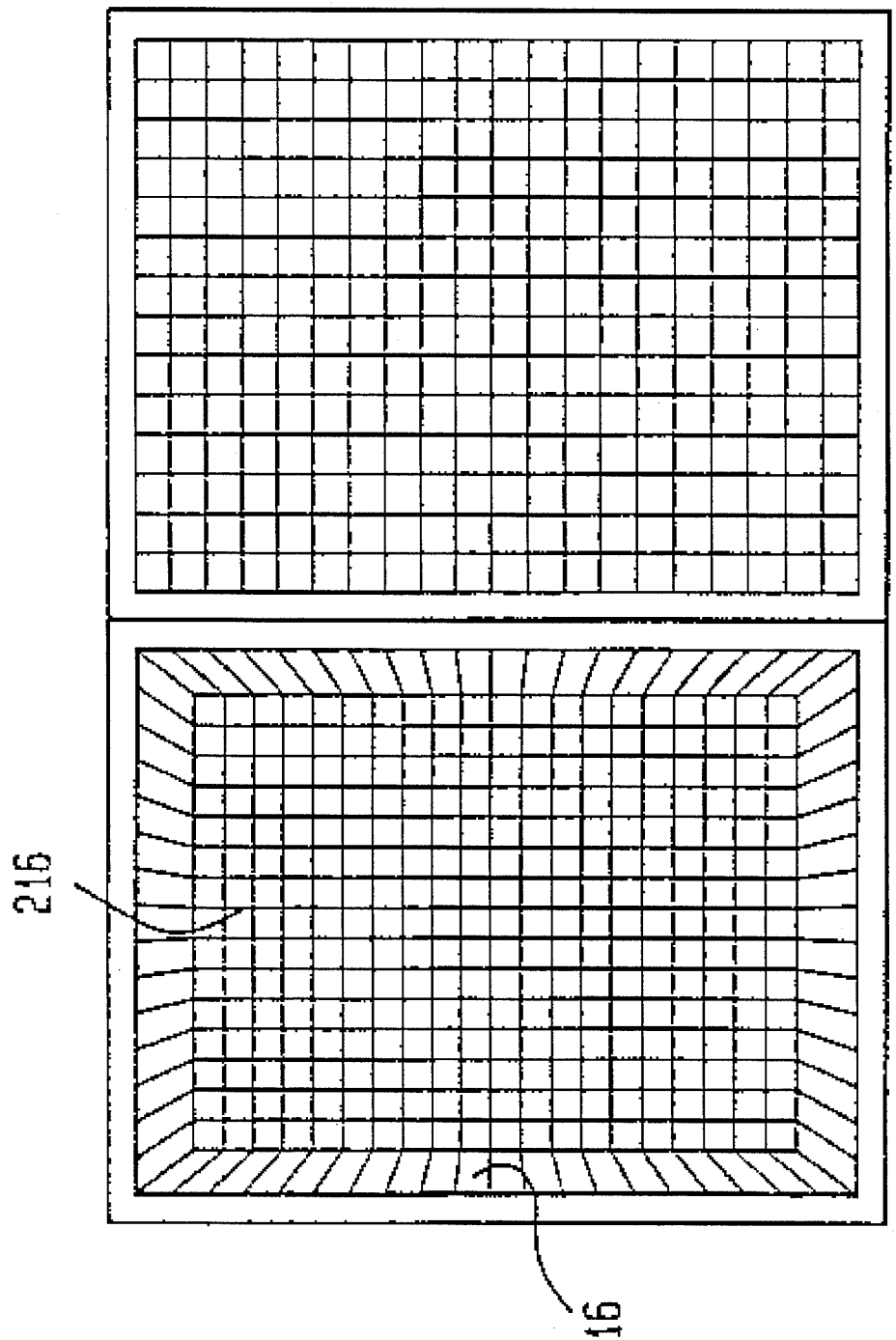
FIG. 5 is a top view of the opened-up pre-amp box of the light gauge of FIG. 1.

The diode end of cylinder 15 supports a flat rectangular box 16 about 95 millimeters long, about 75 millimeters wide, and about 18 millimeters deep which is also constructed from opaque black plastic like blade 25 or of aluminum. This box 16 can serve at least two functions, one being containing the pre-amp circuit for photodiode 30 and the other being connecting the detector optical fiber 164 depending upon the embodiment employed, and providing a flat surface for the spring attachment assembly 210 to press against while still enabling spring attachment assembly 210 to slide along the surface of box 16 in a plane normal to the compressive force. If the inner surface of box 16 encloses the pre-amp circuit, it is lined with radio frequency (RF) screening 216, as shown in FIG. 5. Preferably, the lid of box 16 is screwed on with screws 17, as shown in FIG. 2(*a*), and FIGS. 3(*a*) and 3(*c*).

Spring attachment assembly 210 should be able to slide relative to the surface of box 16 and hence light gauge assembly 10 in order to accommodate different sizes and shapes of hands, because it is important for the "Velcro" hook and loop fastener 12 straps 5 which are attached to the adjusting screws 29 to press on the knuckles of the patient's hands. If the straps 5 are proximal to the knuckle line, and press down too much on the back of the hand, the straps 5 may restrict the venous return flow. On the other hand, once the straps 5 and adjusting screws 29 are properly adjusted, slippage pad 290, shown in FIGS. 6(*a*) and 6(*b*), disposed on the surface of spring plate 250 which faces the surface of the box 16, prevents slippage of the light gauge 10 relative to the spring attachment assembly 210.

Referring to FIG. 4, the opaque cylinder 14 surrounding the photodiode 30, or detector area 163, prevents the light from the green LEDs 20, or optical fiber ring 162, from leaking directly into the photodiode 30, or detector area 163, without first reflecting off the skin of the palm. The height $h_1$ of cylinder 14 should be sufficient to prevent light leakage, yet should also be proportioned to the height $h_2$ of cylinder 15 so that the light from the green LEDs 20 is not partially eclipsed by cylinder 14 from reaching the area of the skin of the palm being illuminated and examined.

The wrist strap 6, shown in FIG. 9(*a*), is loose-fitting and helps to stabilize light gauge 10 and hold blade 25 against the hand, particularly in the DOWN condition. Wrist strap 6 is attached to blade 25 using "Velcro" hook and loop fastener strip 13. Some patients tend to separate their fingers slightly when their hand is in a relaxed condition, so the blade 25 is provided with a widened portion.

The spring attachment assembly 210 ensures that the clamping forces are substantially equal on both hands, and that the clamping force is sufficient to minimize flexing of the hand, reducing random spaces between blade 25 and the palm of the hand, and yet is not so much as to cause blanching of the skin of the palm due to excessive pressure. Preferably four compression springs 230 are employed, well spaced for stability, shown in FIGS. 1 and 6. Controlling the spring 230 force is important, preferably using a spacer block 240, as shown in FIGS. 8(*a*)–(*c*). In a preferred embodiment, spacer block 240 is about 12.7 millimeters wide which, when placed between the spring plates 250 and 255, produces a force equivalent to the weight of 700 grams when adjusting screws 29 are tightened to produce easy sliding contact of spacer block 240 between spring plates 250 and 255, as indicated by the arrows in FIGS. 8(b) and 8(c).

Stop strips 260 are disposed on spring plate 255 just outside the springs 230 to prevent overcompression, and to give stability when the patient's hands are pressing down on block 220, as shown in FIG. 1.

FIGS. 1, 6, and 8 show two centering pins 280 which extend from spring plate 250, and are disposed inside circular holes 285 about 10 millimeters in diameter which extend through the spring attachment assembly 210 top plate 28 and through spring plate 255. The location of the centering pin 280 within the circular hole 285 tells the operator whether or not the "Velcro" hook and loop fastener 12 straps 5 are pulling evenly and symmetrically. If the centering pins 280 are not centered in the circular holes 285, there is an uneven pull of the straps 5 which can be corrected by sliding the light gauge 10 relative to the spring attachment assembly 210. The centering pins 280, when properly aligned in circular holes 285, assure that the shear force is minimized.

During the strap 5 attachment procedure, the spring attachment assemblies 210 rest on support blocks 220, as shown in FIG. 9(a). The adjusting screws 29 and the tips of the centering pins 280 can extend into slot 225 disposed in support block 220, shown in FIG. 9(b), enabling the spring attachment assembly 210 to sit level on a flat surface.

Figure 2A:
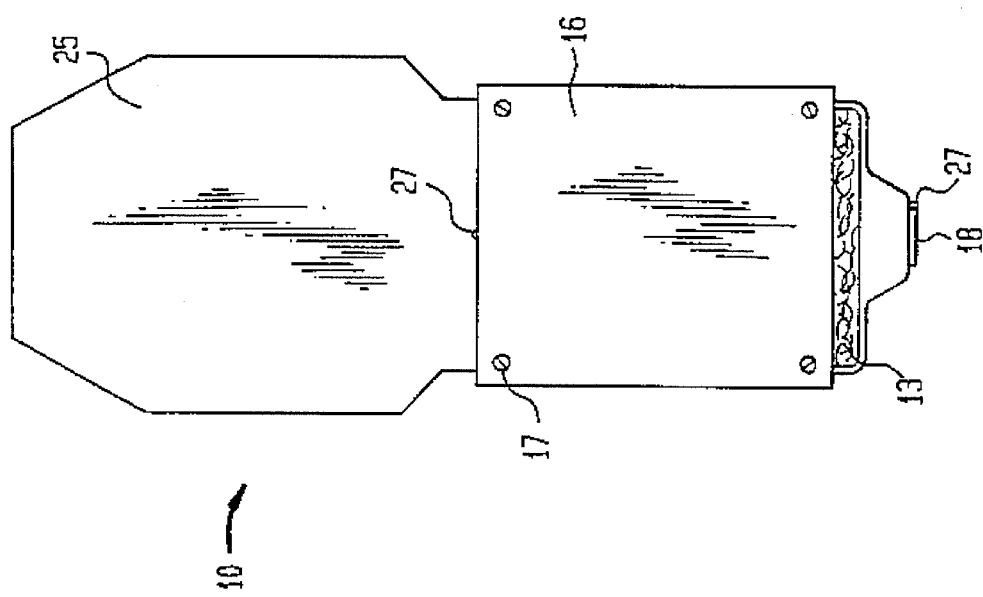

To facilitate correct location of light gauge 10 on the palm, the underside of blade 25 is provided with a locator scale 50, preferably a millimeter scale, shown in FIG. 2(b). As shown in FIGS. 1, and 2(a) and 2(b), indicator diodes 27 are provided on light gauge 10 so that the otherwise indistinguishable light gauges 10 for the left and right hands can be distinguished. For example, in one preferred embodiment of the present invention, the indicator diode 27 for one light gauge 10 is a green LED, and the indicator diode 27 for the other light gauge 10 is a red LED.

Figure 7:
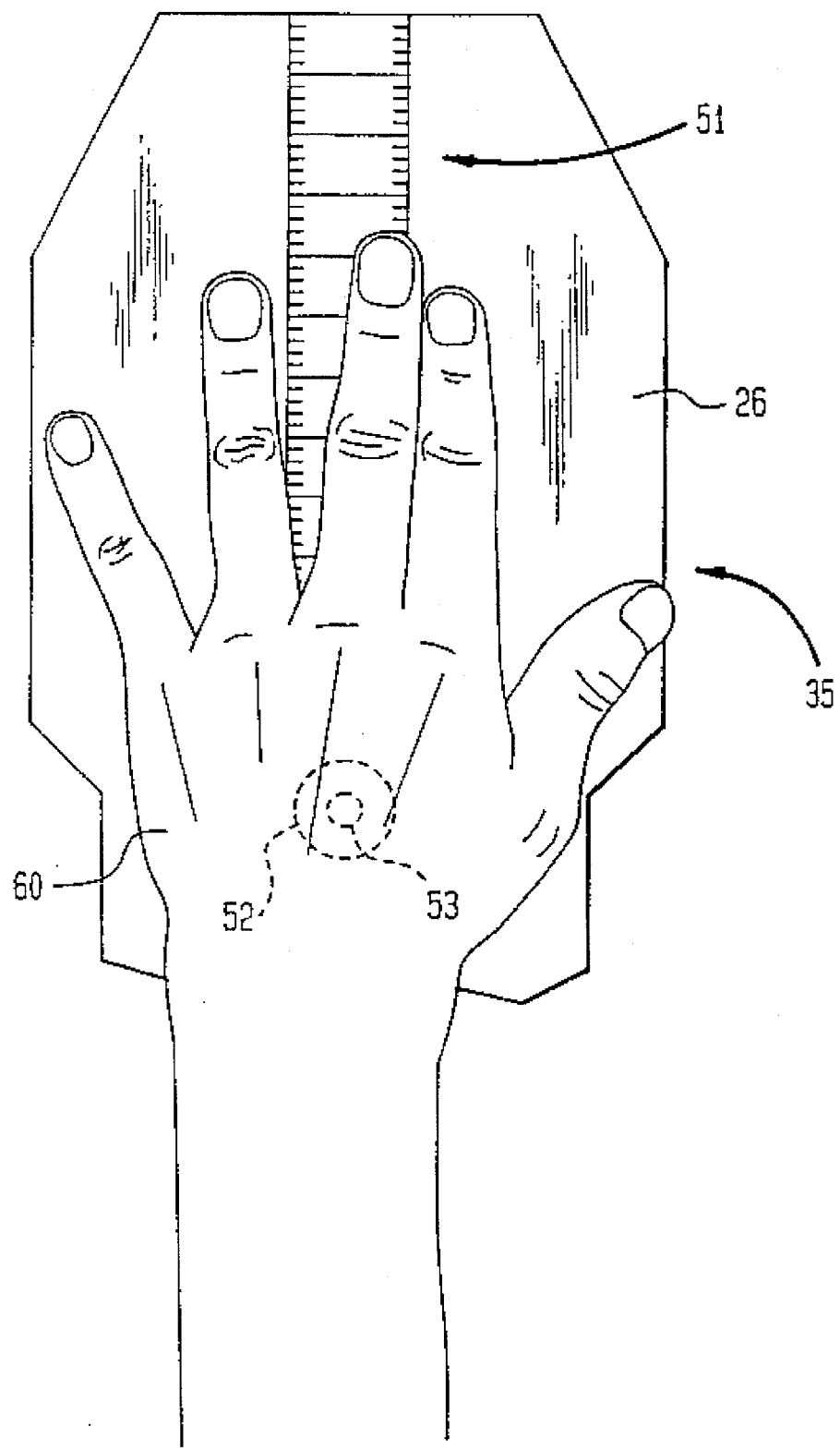
FIG. 7 is a top view of a locator template useful for implementing an embodiment of the present invention.

A top view of locator template 35 is shown in FIG. 7. Template locator scale 51, preferably also a millimeter scale, disposed on transparent plastic template blade 26, corresponds dimensionally to locator scale 50 on the underside of light gauge blade 25. Template blade 26 is also provided with an inscribed circle 52 with a hole in the center, shown in phantom in FIG. 7, having the same diameter as the inner diameter of the black plastic cylinder 15. Left hand 60 is shown in FIG. 7 pressed flat against template blade 26 so that the operator can properly align the inscribed circle 52 with the appropriate position on the palm of hand 60, and the position of the tip of the middle finger is measured, preferably to within a millimeter, against template locator scale 51. Then, when the palm of hand 60 is pressed flat against light gauge blade 25, the same position for the tip of the middle finger can be determined, preferably to within a millimeter on light gauge scale 50, and black plastic cylinder 15 will be appropriately positioned on the palm of hand 60. Straps 5 can fasten the correctly positioned hand 60 to light gauge 10 using the "Velcro" hook and loop fasteners 12.

A system using two light gauges 10 according to a preferred embodiment of the present invention is shown schematically in FIG. 10. Controller cables 7 connect, through connectors 18 shown in FIGS. 2(a), 2(b), 3(b), and 3(c), the light gauges 10 to controller 70, and controller 70 is in turn connected by cable 75 to processor 80, which may be any IBM-compatible or Apple-compatible personal computer, or the like, allowing monitoring with monitor 85 and overall control of the system. Controller 70 has four multiturn precision resistance pots 71 controllable by an operator (not shown). One resistance pot 71 sets the 0% gain setting for a first light gauge 10, a second resistance pot 71 sets the 100% gain setting for the first light gauge 10, a third resistance pot 71 sets the 0% gain setting for a second light gauge 10, and a fourth resistance pot 71 sets the 100% gain setting for the second light gauge 10. There can be other screwdriver adjustable resistance pots (not shown) that are not as readily controllable by the operator, for setting the voltage applied to the green LEDs 20 or incandescent lamp 160, and the like.

An analog to digital (A-to-D) converter 95 is connected by cable 75 to controller 70 and to processor 80 for digital sampling of signals. Analog signals from the light gauge 10 pre-amps in boxes 16 are sent, through connectors 18, through cables 7 to controller 70 and then along cable 75 to A-to-D converter 95 where the analog signals from the left and right light gauges 10 are alternately sampled, with a sampling rate of up to about 7.5 Hz, and preferably of about 3 Hz, and then transmitted in digital form along cable 75 to processor 80.

Calibration of light gauges 10 is effected using dark gray calibration tile 81 and light gray calibration tile 82. The calibration tiles 81 and 82 are maintained approximately at skin temperature, for example, about 30° to 34° C. In a preferred embodiment, calibration tiles 81 and 82 are maintained at a temperature of about 32° C. using temperature controller 97, an independent subsystem which includes an independent 110 V power source, resistance elements for heating calibration tiles 81 and 82, temperature sensors, and maximum temperature cut-offs, for emergency purposes. The heat produced by the hands should be comparable to the heat of the calibration tiles 81 and 82. Alternatively, temperature controller 97 can be connected through controller 70 to processor 80.

Heating the calibration tiles 81 and 82 results in less calibration drift. It is believed that without preheating the calibration tiles 81 and 82, moisture from the patient trapped in the cylinders 15 of the light gauges 10 can condense on the calibration tiles 81 and 82 and possibly on the optical parts of the light gauge 10. The resulting layer of moisture on the calibration tiles 81 and 82 and elsewhere can influence the reflectance measurement, and thus the calibration result. Alternatively, to improve the calibration result, air can be blown into the cylinder to remove the moisture prior to calibration.

Barometric pressure is measurable by using a recording barometer 96. Barometric pressure is entered by the keyboard of processor 80 when the program prompts the operator to enter the barometric pressure by looking at the barometer 96 recording and eyeballing the average barometric pressure over a period of time, preferably over the prior four hours. Alternatively, a manometer 96 can be used that is connectable to processor 80.

Figure 12A:
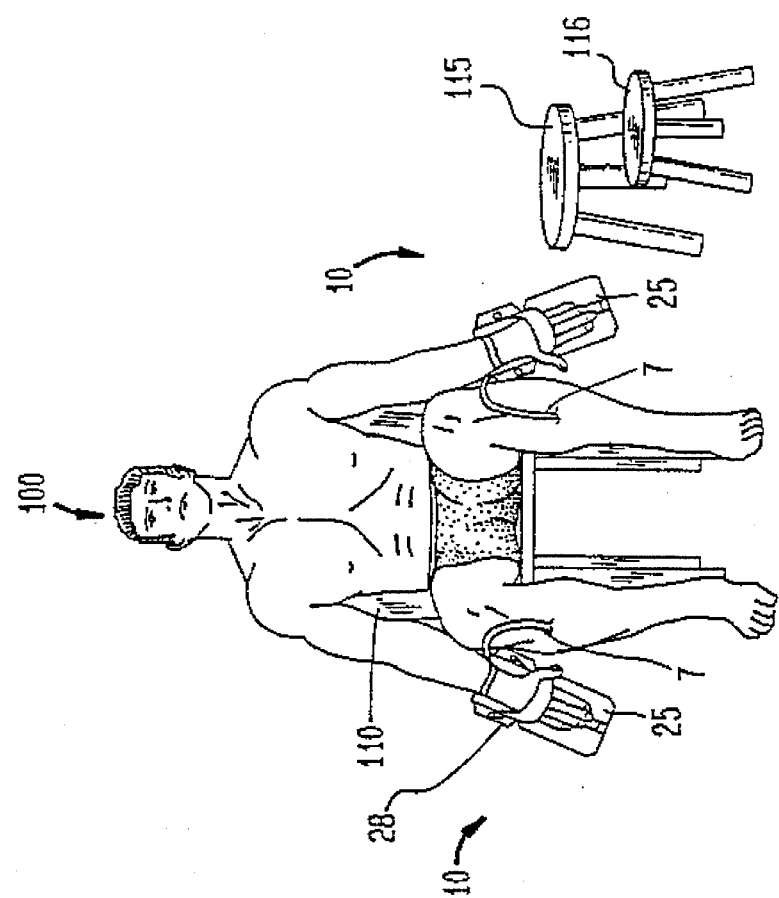
FIGS. 12(a) and 12(b) are perspective views of an embodiment of the present invention in operation with a seated human patient.
Figure 12B:
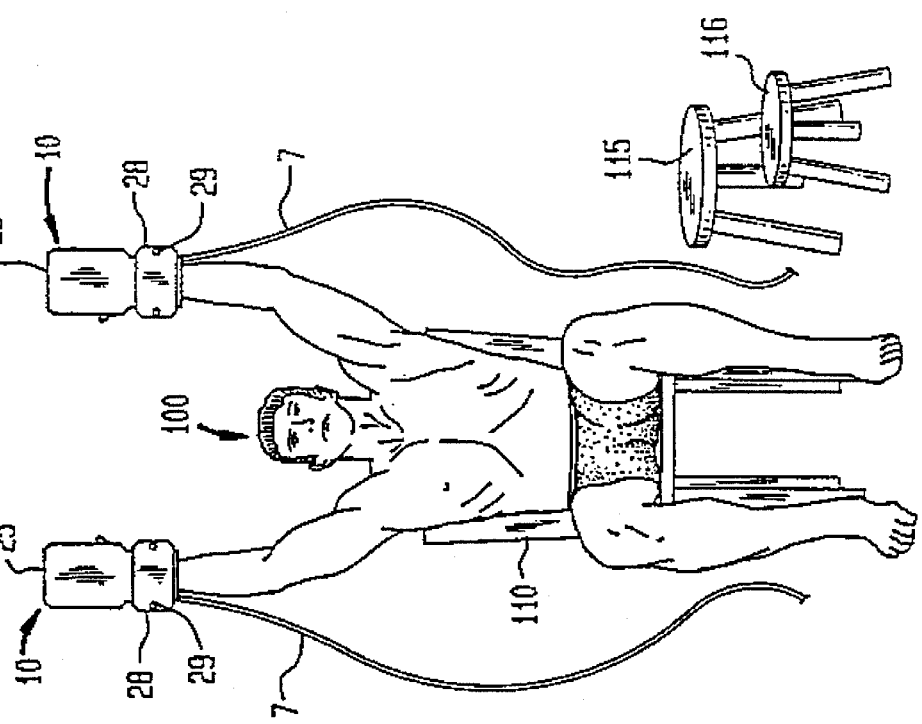

In operation, referring to FIG. 11, and FIGS. 12(a) and 12(b), light gauges 10 are strapped onto the palms of the hands of human patient 100 using locator template 35 and straps 5 with hook and loop fasteners 12 as described above. Both hands are substantially simultaneously raised to the UP condition, as indicated in FIG. 11 in solid lines, and as shown in FIG. 12(a). A padded support 90 for the arms can be used to help stabilize the arms when the patient is unable to hold his hands UP without help, especially since the raised UP condition must be maintained long enough for the readings of the light gauges 10 to stabilize, which usually takes around a minute and a half. If necessary, the arms may be supported by resting them on padded supports 90, as shown in FIG. 11, with elbows bent and forearms substantially vertical. Alternatively, a technician can grasp the patient's wrists to help the patient maintain his hands in the raised UP condition, if necessary. Preferably, as shown in FIGS. 12(a) and 12(b), the patient is sitting up straight in a chair 110, with the hips and back of the patient preferably in contact with and fully supported by the chair 110 back. A selection of stools 115 and 116 can be used so that the feet of the patient may be fully supported, and so that the chair edge does not press unduly on the back of the thighs of the patient. Alternatively, the patient can be standing during the procedure.

The light gauges 10 are held UP as high as comfortable without stretching. It is better to sacrifice two or three centimeters in elevation in order to avoid locking the elbows and shoulders of the patient, and thus possibly impeding the blood flow to and from the extremities. The operator must take care to ensure that the light gauges 10 are at substantially the same elevation. The breathing of the patient should be as normal and regular as possible. The palms can face out as shown, or toward each other, depending on which is the most natural and comfortable position for the patient. As mentioned above, the padded supports 90 are used for patients who have great difficulty holding their arms in an UP condition. The padded supports 90 are preferably soft and well padded, and preferably cover a considerable area under the arms in order to minimize as much as possible impeding venous returns. The arms and hands of the patient are preferably as relaxed as possible.

Measurements are taken after the readings of the light gauges 10 have substantially stabilized, and also while the readings are stabilizing, and while the patient is breathing substantially uniformly with both of his hands raised in the UP condition at substantially the same height above a reference elevation, for example, above the floor, or, alternatively, above a line formed by the shoulders of the patient. Measurements are taken every $\tau$ seconds (where $\tau$ may be about ⅓ second) in the raised UP condition for about a minute, or, alternatively, for about a minute and a half, and then the arms are substantially simultaneously lowered to the DOWN condition, as indicated in FIG. 11 in phantom lines, and as shown in FIG. 12(b). Alternately sampling the left and right signals gives an individual channel rate of between 3 to 7 cycles/sec. when using a partially mechanical A-to-D converter or a higher rate when using an electronic A-to-D converter, which also depends on the size of the channel count. The higher the count rate, the better the resolution. The readings of the light gauges 10 are allowed to stabilize which usually takes about two to three minutes. The arms of the patient when in the lowered DOWN condition are unsupported.

Both feet of the patient should be flat on the floor, or on an appropriately high stool, such as 115 or 116, in order to prevent venous returns in the thighs from being retarded. Both arms of the patient should be completely relaxed, essentially just dangling, an important aspect of the operation of the present invention. As mentioned above, the hips and back of the patient are preferably in contact with and fully supported by the chair 110 back. The whole body of the patient should be relaxed as much as possible. The hands and arms of the patient are therefore preferably as relaxed as possible throughout the test procedure, both in the UP and DOWN conditions.

Measurements are taken after the readings of the light gauges 10 have substantially stabilized, and also while the readings are stabilizing, and while the patient is breathing substantially uniformly with both of his hands lowered in the DOWN condition at substantially the same height above a reference elevation, for example, above the floor, or, alternatively, below a line formed by the shoulders of the patient, the absolute height being relatively unimportant as long as the arms just dangle. Measurements are taken every $\tau$ seconds (where $\tau$ is about ⅓ second) in the lowered DOWN condition for about a minute, or, preferably, for about two to three minutes, and then the arms are substantially simultaneously raised back to the UP condition, as indicated in FIG. 11 in solid lines, and as shown in FIG. 12(a). The readings of the light gauges 10 are allowed to stabilize which usually takes about two to three minutes.

This process of alternating measurements taken in the raised UP condition and the lowered DOWN condition is iterated until a sufficient number of complete UP and DOWN cycles have been recorded to provide reliable results. In a preferred embodiment, three complete UP and DOWN cycles are recorded, with measurements made starting with both arms in the raised UP condition, continuing with both arms in the lowered DOWN condition, alternating UP and DOWN twice more, and then ending with both arms in the raised UP condition.

Because of inevitable differences between the two light gauges 10 used, combined with variations in the attachments of the light gauges 10 to the different hands, coupled with the normal differences in the right and left hands of the patient, and in order to eliminate possible systematic errors in the measurement process, after a complete set of UP and DOWN measurements are taken with the light gauges 10 in a first or normal configuration, another identical set of UP and DOWN measurements are taken with the light gauges 10 in a second or reversed configuration. The light gauge 10 (red LED 27, for example) that was attached to the patient's right hand in the first or normal configuration is attached to the patient's left hand in the second or reversed configuration, and the light gauge 10 (green LED 27, for example) that was attached to the patient's left hand in the first or normal configuration is attached to the patient's right hand in the second or reversed configuration. Thus, a series of several complete sets of UP and DOWN measurements are taken with the light gauges 10 in the first or normal configuration, followed by another series of several complete sets of UP and DOWN measurements taken with the light gauges 10 in the second or reversed configuration. In a preferred embodiment, a total of three normal followed by three reversed configurations are used for a complete test which takes about 25 to 30 minutes to administer to the patient.

Figure 13:
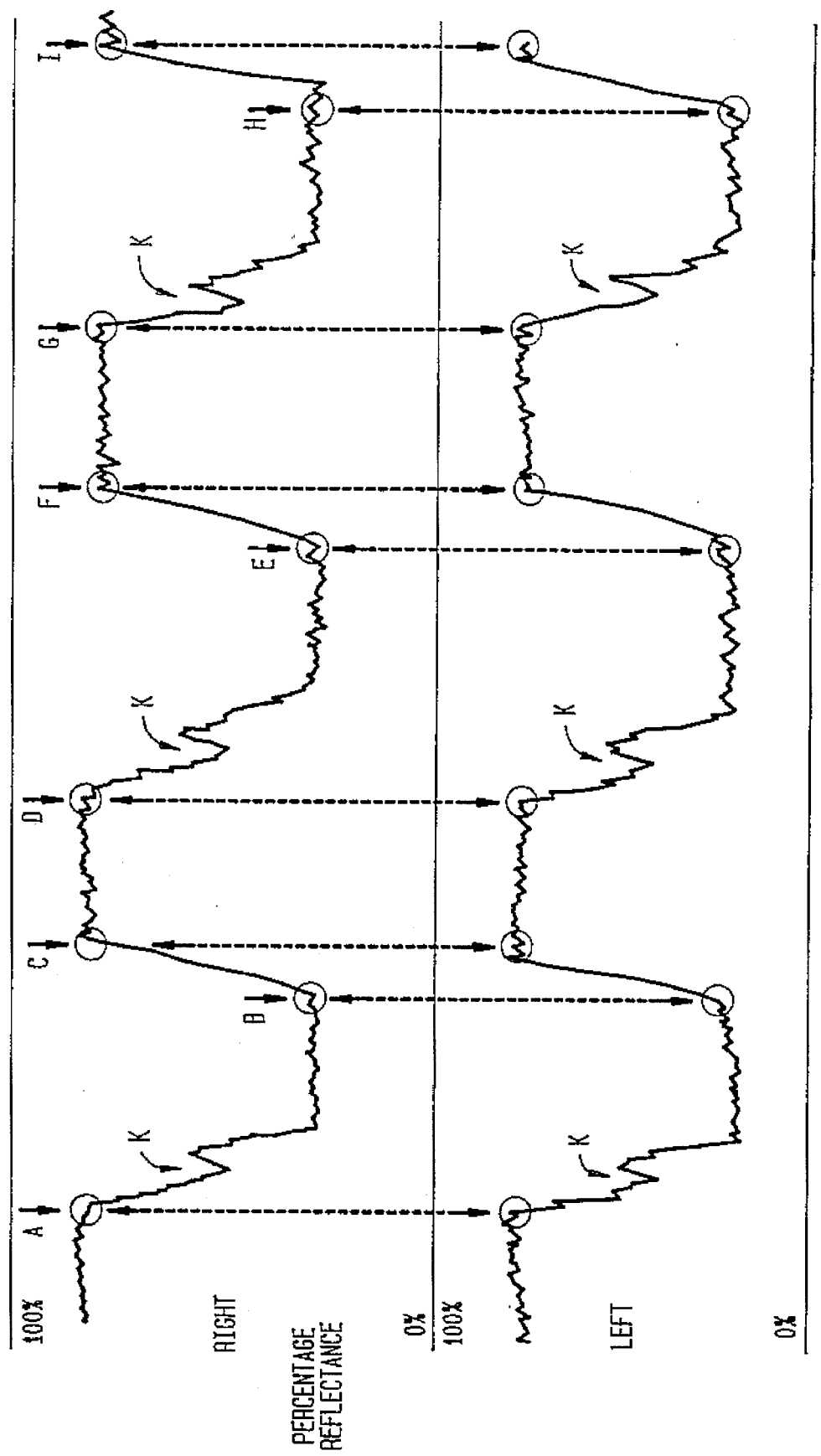
FIG. 13 is representative of a portion of an output observable on the monitor of an embodiment of the present invention.

The light gauges 10 are individually calibrated by placing them on standardized dark gray 81 and light gray 82 calibration tiles shown in FIG. 10. Photodiode light detector 30 is looking at a dark gray field relative to a standardized gray scale. The reflectance of the green LED 20 light from light gray calibration tile 82 is set to the value of 100% reflectance, and the reflectance of the green LED 20 light from dark gray calibration tile 81 is set to the value of 0% reflectance. These standardized light gray and dark gray colors are preferable because they are reasonably close to, but usually outside the range of, all patients tested. In other words, the dark gray calibration tile 81 is below the color of the palms in the DOWN condition of all patients, and is designated as and defined to be 0% reflectance. Alternatively, a red tile can be designated as and defined to be 0% reflectance. The light gray calibration tile 82 is above the color of the palms in the UP condition of substantially all patients tested, and is arbitrarily designated as and defined to be 100% reflectance. Consistency in calibration colors is more important than absolute color reflectance values output since usually only color reflectance value differences are employed in substantially all the calculations. As mentioned above, the percentage reflectance from the palms of the hands will usually fall between 0% reflectance and 100% reflectance, as shown in FIGS. 13, 14, and 15 which illustrate outputs representative of what a skilled operator would observe on monitor 85 during and after a measurement cycle.

The operator watches the screen of the monitor during the testing and judges when the readings are sufficiently stabilized. The operator also monitors a number of parameters, preferably six, that relate algebraically to the percentage reflectances. One of the parameters monitored, for example, is the running difference R-L, where R is the instantaneous percentage reflectance measured by the light gauge 10 on the right hand, and where L is the instantaneous percentage reflectance measured by the light gauge 10 on the left hand. Other monitored parameters, for example, are R, L, dR/dt and dL/dt, where dR/dt is the instantaneous rate of change of R with time, and dL/dt is the instantaneous rate of change of L with time. A sixth preferably monitored parameter is the running UP-DOWN differential RIGHT-LEFT difference $\Delta_{R-L}$:

$$\Delta_{R-L}=(R_U-R_D)-(L_U-L_D)=\Delta_R-\Delta_L$$

where the running $\Delta_{R-L}$ is used as a guide for the operator since, as is explained in more detail below, the more accurate calculations of $\Delta_{R-L}$ are made using critical points which the operator identifies on the measurement tracings after the testing run is completed.

A series of these values are determined for the light gauges 10 in the normal configuration, in the reversed configuration. The average of these values is also determined, the average between the values calculated for the UP and DOWN series may also be calculated, as well as the difference between the UP and DOWN measurements.

The operator observes the readings on the screen of the monitor 85 and places critical points, such as A-I in FIG. 13, on the image. A blown-up or magnified image of the critical regions in the neighborhoods of critical points such as A through I can be used for better accuracy in the placement of the critical points A through I.

Rather than have the computer 80 calculate the differential RIGHT-LEFT difference, the operator can simply observe the difference values, optionally with the aid of a scale overlaid on an image such as shown in FIGS. 13 and 14. The inventive method does not require any mathematics, but greater accuracy is achieved by performing the simple subtraction steps, i.e., finding the delta values mentioned above. One can compare measurements obtained with the patients hands in a raised, steady-state condition with measurements obtained in the lowered, steady-state condition to determine cardiovascular conditions by any suitable fashion, including simply eyeballing a graphic display such as shown in FIGS. 13 and 14, determining numeric values for the measurements and comparing the relative values, or comparing the numeric values by simple subtraction steps. In and embodiment using subtraction steps, to a degree it matters not which of the different values are subtracted from one another, so long as there is a standard for comparison. For instance, subtracting the UP values from the DOWN values gives positive numbers as results, but the DOWN values could be subtracted from the UP values. To illustrate that the invention does not require mathematics of any kind, it is possible that the graphs shown in FIGS. 13 and 14 could be divided up into levels to which are assigned letters, and the combination of letters resulting from a comparison could be used to determine vasomotor tone. This would be awkward at best. The point is, so long as the technique actually employed results in a meaningful comparison between the vasomotor tone of the right and left extremities in raised and in lowered positions, the objects of the invention can be achieved. Simple subtraction is used in the examples below.

The proper positioning of the critical points is important. In a preferred embodiment, the print-out of a complete testing run (usually 6 complete cycles of UP and DOWN measurements, 3 normal and 3 reversed) is usually condensed to a 15.25 centimeter field, as shown in FIGS. 14 and 15. However, as mentioned above, for the purpose of accuracy in locating the critical points, the field is magnified horizontally on the display and/or on the print-out by a magnification factor of about five times (5×). Some skill on the part of the operator is required in proper critical point placement. FIGS. 14 and 15 illustrate typical print-outs made after a measurement cycle.

In a preferred embodiment, the calculations are based on the A-B difference values, representing the "filling" of blood that occurs when the arms are lowered to the DOWN condition from the UP condition, as shown in FIG. 14. The B-C difference values are also calculated, representing the "dumping" of blood that occurs when the arms are raised to the UP condition from the DOWN condition, as shown in FIG. 15. In order to improve the accuracy of the calculations, the processor 80 averages all previous data points for a specific period prior to the critical points. Preferably about 25 data points are usually enough to smooth out the calculation. Occasionally up to 100 or more data points are averaged.

The option of adjusting the recorded field vertically is also provided in a preferred embodiment. This vertical adjustment option is used to compensate for the lightness or darkness of the skin of the patient. This vertical adjustment option does not affect the accuracy since the calibration as well as the light gauge 10 reflectance value output are all moved up or down proportionately.

In general, once critical points, such as A through I, have been placed on the tracings, with corresponding critical points on the RIGHT and LEFT tracings shown by dotted doubleheaded arrows in FIG. 13, the percentage reflectance values are averaged over preferably about 25 previous discrete values (one discrete value occurring every τ seconds, where τ is about ⅓ second, depending on the digital sampling rate and/or the A-to-D converter 95 conversion rate) to give the averaged percentage reflectance values that are used in computing the indications of relative vasomotor tone, determining whether vasomotor tone is above or below normal.

Referring to FIG. 14, the critical points that are useful for calculating the blood "filling" measurements are labelled with their respective percentage reflectance values, averaged over the previous 25 data points. The first difference value Diff is $\Delta_{R-L}^{Nor}$=2.13, corresponding to A-B in FIG. 13 in the normal configuration of the light gauges, the second difference value Diff is $\Delta_{R-L}^{Nor}$=1.88 corresponding to D-E in FIG. 13 in the normal configuration of the light gauges, and the third difference value Diff is $\Delta_{R-L}^{Nor}$=1.38, corresponding to G-H in FIG. 13 in the normal configuration of the light gauges. Similarly, the fourth difference value Diff is $\Delta_{R-L}^{Rev}$=1.69, corresponding to A-B in FIG. 13 in the reversed configuration of the light gauges, the fifth difference value Diff is $\Delta_{R-L}{}^{Rev}=1.38$, corresponding to D-E in FIG. 13 in the reversed configuration of the light gauges and the sixth difference value Diff is $\Delta_{R-L}{}^{Rev}=2.81$, corresponding to G-H in FIG. 13 in the reversed configuration of the light gauges.

The DX values in FIG. 14 represent the areas under the curves in between the Right and Left tracings, which curves represent the running difference between the Right and Left tracings between consecutive UP and DOWN critical points. The averaged DX values can be used to be indicative of overall vasomotor tone similar to the manner in which $\Delta_{R-L}{}^{Ave}$ values are used to determine whether overall vasomotor tone is above or below normal.

The values in the Normal and Reversed columns in FIG. 14 are averages of the three respective critical points. The values in the Average column are the average of the respective values in the Normal and Reversed columns, and the values in the Difference column are the difference between the respective values in the Normal and Reversed columns. The key value is Average R-L Delta, $\Delta_{R-L}{}^{Ave}=1.8750$ which is a very sensitive final result, corresponding to about +2 percentage reflectance values. If the two light gauges were substantially identical and were substantially identically attached to the hands, the values in the Difference column would all be zero.

Referring to FIG. 15, the critical points that are useful for calculating the blood "dumping" measurements are labelled with their respective percentage reflectance values, averaged over one data point. The first difference value Diff is $\Delta_{R-L}{}^{Nor}=1.00$, corresponding to B-C in FIG. 13 in the normal configuration of the light gauges, the second difference value Diff is A $\Delta_{R-L}{}^{Nor}=-1.06$, corresponding to E-F in FIG. 13 in the normal configuration of the light gauges, and the third difference value Diff is $\Delta_{R-L}{}^{Nor}=-0.44$, corresponding to H-I in FIG. 13 in the normal configuration of the light gauges. Similarly, the fourth difference value Diff is $\Delta_{R-L}{}^{Rev}=1.06$, corresponding to B-C in FIG. 13 in the reversed configuration of the light gauges, the fifth difference value Diff is $\Delta_{R-L}{}^{Rev}=0.94$, corresponding to E-F in FIG. 13 in the reversed configuration of the light gauges, and the sixth difference value Diff is $\Delta_{R-L}{}^{Rev}=1.63$, corresponding to H-I in FIG. 13 in the reversed configuration of the light gauges.

The DX values in FIG. 15 represent the areas under the curves in between the Right and Left tracings, which curves represent the running difference between the Right and Left tracings between consecutive UP and DOWN critical points. The averaged DX values can be used to be indicative of overall vasomotor tone similar to the manner in which $\Delta_{R-L}{}^{Ave}$ values are used to determine whether overall vasomotor tone is above or below normal.

The values in the Normal and Reversed columns in FIG. 15 are averages of the three respective critical points. The values in the Average column are the average of the respective values in the Normal and Reversed columns, and the values in the Difference column are the difference between the respective values in the Normal and Reversed columns. The key value is Average R-L Delta, $\Delta_{R-L}{}^{Ave}=0.5208$, which Is a very sensitive final result, corresponding to about +½ percentage reflectance values. Again, if the two light gauges were substantially identical and were substantially identically attached to the hands, the values in the Difference column would all be zero.

The final values obtained may be compared with the manual palpitation of the right and left radial pulse technique mentioned above, revealing that a value of $\Delta_{R-L}{}^{Ave}=-10$ correlates reliably and reproducibly with a severely low or dilated vasomotor tone, whereas values of $\Delta_{R-L}{}^{Ave}$ in the range of −2 to −5 correlate reliably and reproducibly with a less severely low or dilated vasomotor tone Correspondingly, a value of $\Delta_{R-L}{}^{Ave}=+10$ correlates reliably and reproducibly with a severely high or constricted vasomotor tone, whereas values of $\Delta_{R-L}{}^{Ave}$ in the range of +2 to +5 correlate reliably and reproducibly with a less severely high or constricted vasomotor tone.

The manual method and the Erdman Indicator method, i.e., the method of the present invention, complement each other. The manual method only takes a few seconds, and is used by an expert practitioner many times during the course of a single treatment. The method of the present invention, on the other hand, takes up to about 30 minutes to administer, may be easily practiced by any skilled operator without requiring the presence of an expensive expert practitioner, produces a hard copy record of the measurements and results, and is repeatably accurate. Alternatively, the method of the present invention can be practiced by being administered remotely to a patient using mobile light gauges with the measurements transmitted over a modem to a processor at a central location, such as the Erdman Clinic, where the measurements are analyzed yielding the results of the remote diagnosis.

The Erdman Indicator allows, for the first time, quantitative monitoring of the effectiveness of medical treatments in the raising or lowering of vasomotor tone. For example, by running a test using the Erdman Indicator on a patient both before and after dosing the patient with antibiotics, a quantitative measurement of the effect of the antibiotics on the patient's vasomotor tone can be made. Similarly, the effects on overall vasomotor tone of diet, nutrition, vitamin programs, and/or exposure to ultraviolet radiation can be quantitatively monitored by testing the patient both before and after using the Erdman Indicator.

Trial and error throughout experimental testing of the Erdman Indicator have revealed the importance of the following points for the successful practice of a preferred embodiment of the principles of the present invention:

- The patient should wash his hands in warm water before starting the test.
- The selection of the chair 110 is important in order to allow the arms of the patient to dangle in a DOWN condition, and in order to support the back of the patient throughout the test.
- A selection of stools 115 and 116 is needed so that the feet of the patient may be fully supported, and so that the chair edge does not press unduly on the back of the thighs of the patient.
- The patient is instructed on the testing procedures, for example, three full UP and DOWN cycles with the light gauges 10 in the normal configuration followed by three more UP and DOWN cycles with the light gauges 10 in the reversed configuration.
- The breathing of the patient should be as regular and uniform as possible. A big breath can influence the measurement readings by as much as 10 percentage reflectance values.
- The test is run in subdued lighting so as to minimize stray light leaking in and disrupting the readings.
- The patient should remain as relaxed as possible throughout the run. A pleasant seascape, or the like, can be provided for the patient to look at during the run. Talking is discouraged, and the patient does not see the monitor 85 screen during the run. In experimental tests run so far, there has not been any evidence observed of biofeedback. Keeping the attention of the patient on pleasant things, and not worrying about the test results are desirable.

The attachment of the gauges to the hands is a finely tuned procedure which gives good reproducible results.

The operator instructs the patient as to when and how to change from UP to DOWN to UP, and so forth. The criteria in substantially every case is to wait until the color has stabilized. Skill and training on the part of the operator is essential. The information provided by the various digital displays of monitored parameters is of great help in this regard.

Preferably, the light gauge 10 calibration is checked at the start of the run, whenever the light gauges 10 are reversed, and again at the end of each run. In a preferred embodiment, a temperature compensated pre-amp circuit minimizes the amount of gauge drift. The software program incorporates an automatic means of distributing any gauge drift uniformly over several UP-DOWN extremity position cycles. For instance, at the end of three cycles, a measured gauge drift of 6 mV can be distributed over the three cycles by assigning a drift of 0 mV to the first cycle, 3 mV to the second cycle and 6 mV to the third cycle based on the assumption that the drift is uniform over time and thereby distributed uniformly over time.

In a preferred embodiment, as many as 58 different parameters are automatically calculated by the processor 80, and printed out on the run of each patient, as in FIGS. 14 and 15. Several other parameters are also usefully entered into the record such as:

1) The kind of treatment, if any, received during the two hours prior to the test.
2) The barometric pressure.
3) The blood pressure (systolic, diastolic, and pulse).
4) The pulse rate.
5) The time of the start of the most recent meal.
6) The location of the light gauges 10 on the hands.
7) Whether the use of arm supports 90 is required.
8) The preheat temperature of the light gauges 10.
9) The name of the operator.
10) The date and location of the test.

Preferably, graphs can be printed out of any desired combination of over 60 of the parameters such as those given above, or of any single parameter, plotted against run number or the date of the run.

The principles, preferred embodiments and modes of operation of the present invention have been described in the foregoing specification. The invention which is intended to be protected herein, however, is not to be construed as limited to the particular forms disclosed, since these are to be regarded as illustrative rather than restrictive. Moreover, variations and changes may be made by those skilled in the art without departing from the spirit of the present invention.

For example, another embodiment of the present invention provides a sensor for measuring a physical parameter indicative of relative blood flow or pooling, such as a temperature sensor or a strain gauge instead of the light gauge described hereinabove. Alternatively, a green filter that filters a white light source can be used in place of the above-described green LEDs. Similarly, a red standardized tile can be used in place of the above-described dark gray standardized tile.

Yet another preferred embodiment uses two sets of sensors fixedly mounted in the UP and DOWN conditions, respectively, instead of being removably attached to the hands. The hands are then simply moved sequentially from the UP condition to the DOWN condition for as many cycles as are desired, with the hands being pressed against the respective sensor surfaces with substantially equal force.

Alternative embodiments provide a "Velcro" hook and loop fastener strap surrounding both hands with the light gauges in place on the palms with the palms of the hands facing each other, and with a compressible spacer between the light gauges, thereby ensuring that the clamping force is the same on both hands. In this embodiment, the hands can be lowered to about lap level for the DOWN condition, and a pulley arrangement attached to the ceiling can be used to assist the patient in holding the hands in the UP condition. Other embodiments use pneumatic bladders connected together to the same pressure source to generate the desired application force instead of, or in addition to, the spring attachment assembly above-described. The number and spring constants of the compression springs can be varied, and/or a tension spring device can be used. Strain gauges and/or displacement measuring devices, and/or remotely recording on a strip chart the force applied to the light gauges by measuring displacement can all be used to control the spring force. Yet another alternative embodiment provides that the spring attachment assemblies remain removably attached to the same hands in both the normal and reversed configurations with only the diode cylinders and/or pre-amps being interchanged between the normal and reversed configurations.

Alternative embodiments of the present invention can sense the differential and/or relative blood flow and/or pooling of the carotid arteries to either side of the neck, the earlobes, the supraorbital notches above the eyes, and/or the temples. Any differential and/or relative blood flow and/or pooling to the lower extremities can be sensed in alternative embodiments. The present invention is particularly advantageous when used to sense the differential and/or relative blood flow and/or pooling between body regions with an asymmetrical blood supply, such as the upper extremities.

Therefore, the present invention should not be regarded as being limited to the specific embodiments disclosed herein, but instead should be regarded as being fully commensurate in scope with the following claims. Furthermore, any element in the following claims expressed as a means or step for performing a specified function without the recital of structure, material, or acts in support thereof shall be construed to cover the corresponding structure, material, or acts described herein and equivalents thereof.

What is claimed is:

1. A method of determining cardiovascular conditions comprising the steps of:

removably attaching a sensor to a surface of each of a pair of extremities of a patient for measuring a physical parameter indicative of cardiovascular conditions;

measuring said parameter substantially simultaneously on both extremities while both extremities are in a raised, steady-state condition;

measuring said parameter substantially simultaneously on both extremities while both extremities are in a lowered, steady-state condition;

comparing the measurements obtained in the raised, steady-state condition with the measurements obtained in the lowered, steady-state condition to determine cardiovascular conditions; and recording the result of said comparing step.

2. A method in accordance with claim 1, wherein said surface of each of a pair of extremities is the palm of each hand of a patient.

3. A method in accordance with claim 2, wherein each sensor exerts a substantially equal force on each palm.

4. A method in accordance with claim 1, further including performing said steps of attaching said sensors, measuring said parameter while extremities are in said raised condition, measuring said parameter while extremities are in said lowered condition, and comparing said measurements with said sensors in a first orientation relative to respective extremities, said method further comprising repeating said steps of attaching said sensor unit, measuring said parameter while extremities are in said raised condition, measuring said parameter while extremities are in said lowered condition, and comparing said measurements with said sensors in a second configuration which is the reverse of said first configuration, prior to said recording step.

5. A method according to claim 1, further comprising the step of:

calibrating the sensor for measuring the parameter.

6. A method according to claim 5, wherein said step of calibrating the sensor includes removably attaching said sensor to an inanimate object having a known physical parameter.

7. A method according to claim 6, wherein said step of calibrating the sensor further includes maintaining a temperature of said inanimate object at a temperature approximate to that of said patient.

8. A non-invasive method for determining vasomotor tone comprising the steps of:

removably attaching a light sensor unit to a surface of each of a pair of extremities of a patient for measuring a light reflection parameter of each of the extremities;

measuring the light reflection parameter of the surfaces of the extremities substantially simultaneously on both extremities while both extremities are in a raised, steady-state condition;

measuring the light reflection parameter of the surfaces of the extremities substantially simultaneously on both extremities while both extremities are in a lowered, steady-state condition;

comparing the light reflection parameter measurements obtained in the raised, steady-state condition with the light reflection parameter measurements obtained in the lowered, steady-state condition to determine vasomotor tone; and recording the determined vasomotor tone.

9. A method in accordance with claim 8, wherein said surface of each of said pair of extremities is the palm of each hand of a patient.

10. A method in accordance with claim 9, wherein each sensor unit exerts a substantially equal force on each palm.

11. A method in accordance with claim 8, further including performing said steps of attaching said light sensor unit, measuring said parameter while extremities are in a raised condition, measuring said parameter while extremities are in a lowered condition, and comparing said measurements with said light sensor unit in a first configuration, said method further comprising repeating said steps of attaching said light sensor unit, measuring said parameter while extremities are in a raised condition, measuring said parameter while extremities are in a lowered condition, and comparing said measurements with said light sensor unit in a second configuration which is the reverse of said first configuration, prior to said recording step.

12. A method according to claim 8, further comprising the step of:

calibrating the sensor unit for measuring the parameter.

13. A method according to claim 12, wherein said step of calibrating the sensor unit includes removably attaching said sensor unit to an inanimate object having a known physical parameter.

14. A method according to claim 13, wherein said step of calibrating the sensor unit further includes maintaining a temperature of said inanimate object at a temperature approximate to that of said patient.

15. A non-invasive method of determining cardiovascular conditions comprising the steps of:

sensing, at a surface of each of a pair of extremities of a patient, a physical parameter indicative of cardiovascular conditions;

sensing said parameter substantially simultaneously on both extremities while both extremities are in a raised, steady-state condition;

sensing said parameter substantially simultaneously on both extremities while both extremities are in a lowered, steady-state condition;

comparing the sensed parameter obtained in the raised, steady-state condition with the sensed parameter obtained in the lowered, steady-state condition to determine cardiovascular conditions; and recording results of said comparing step.

16. A method according to claim 15, wherein said sensing step is performed by a sensor unit which includes a light gauge and said physical parameter is a light reflection parameter.

17. A method according to claim 16, wherein each sensor unit exerts a substantially equal force on each extremity.

18. A method according to claim 16, further comprising the step of reversing an orientation of the sensor units relative to respective extremities and repeating said steps of attaching said sensor units, measuring said parameter while both extremities are in said raised condition, measuring said parameter while both extremities are in said lowered condition, comparing the measurements obtained in the raised condition with the measurements obtained in the lowered condition with said sensor units in said reversed orientation prior to recording the results of said comparing step.

19. A method according to claim 16, further comprising the step of:

calibrating the sensor unit for measuring the parameter.

20. A method according to claim 19, wherein said step of calibrating the sensor unit includes removably attaching said sensor unit to an inanimate object having a known physical parameter.

21. A method according to claim 20, wherein said step of calibrating the sensor unit further includes maintaining a temperature of said inanimate object at a temperature approximate to that of said patient.

22. In an Erdman Therapy method to improve blood flow rates for patients with high vasomotor tone through application of heat, massage, or ultrasound therapies, and to improve blood flow rates for patients with low vasomotor tone through cold applications on spinal muscles or on portions of spinal muscles, the improvement comprising the steps of:

removably attaching a sensor unit to a surface of each of a pair of extremities of a patient for measuring a physical parameter indicative of cardiovascular conditions;

measuring said parameter substantially simultaneously on both extremities while both extremities are in a raised, steady-state condition;

measuring said parameter substantially simultaneously on both extremities while both extremities are in a lowered, steady-state condition;

comparing the measurements obtained in the raised, steady-state condition with the measurements obtained in the lowered, steady-state condition; and implementing a therapy based on the results of said comparing step.

23. A method according to claim 22, wherein said sensor unit includes a light gauge and said physical parameter is a light reflection parameter.

24. A method according to claim 22, further comprising the step of recording said result of said comparing step.

25. A method according to claim 22, wherein each sensor unit exerts a substantially equal force on each extremity.

26. A method according to claim 22, further comprising the step of reversing an orientation of the sensor units relative to respective extremities and repeating said steps of attaching said sensor units, measuring said parameter while both extremities are in said raised condition, measuring said parameter while both extremities are in said lowered condition, comparing the measurements obtained in the raised condition with the measurements obtained in the lowered condition with said sensor units in said reversed orientation prior to implementing the therapy based on the results of said comparing step.

27. A method according to claim 22, further comprising the step of:

calibrating the sensor unit for measuring the parameter.

28. A method according to claim 27, wherein said step of calibrating the sensor unit includes removably attaching said sensor unit to an inanimate object having a known physical parameter.

29. A method according to claim 28, wherein said step of calibrating the sensor unit further includes maintaining a temperature of said inanimate object at a temperature approximate to that of said patient.

30. In an Erdman Therapy method to improve blood flow rates for patients with high vasomotor tone through application of heat, massage, or ultrasound therapies, and to improve blood flow rates for patients with low vasomotor tone through cold applications on spinal muscles or on portions of spinal muscles, the improvement comprising the steps of:

sensing, at a surface of each of a pair of extremities of a patient, a physical parameter indicative of cardiovascular condition;

sensing said parameter substantially simultaneously on both extremities while both extremities are in a raised, steady-state condition;

sensing said parameter substantially simultaneously on both extremities while both extremities are in a lowered, steady-state condition;

comparing the sensed parameter obtained in the raised, steady-state condition with the sensed parameter obtained in the lowered, steady-state condition; and implementing a therapy based on results of said comparing step.

31. A device comprising:

at least two light sensor units removably attachable to extremities of a patient for measuring a light reflection parameter;

controller means for controlling said light sensor units during the performance of light reflection parameter measurements;

comparing means for comparing a light reflection parameter measurement made substantially simultaneously on two extremities of a patient while both extremities of a patient are in a raised, steady-state condition with a light reflection parameter measurement made substantially simultaneously on both extremities of a patient while both extremities of a patient are in a lowered, steady-state condition; and indicating means for indicating a result of said comparing step.

32. A device according to claim 31, wherein each of said at least two light sensor units includes a light emitter means for emitting light and a light detector means for receiving light.

33. A device according to claim 32, wherein said light emitter means includes a plurality of light emitting diodes.

34. A device according to claim 32, wherein said light emitter means includes an light supplying optical fiber operatively connected to a light emitter located remote to said at least two light sensor units.

35. A device according to claim 32, wherein said light detector means includes an optical fiber operatively connected to receive said light reflection parameter and transmit said light reflection parameter to a light detector located remote to said at least two light sensor units.

36. A device according to claim 31, wherein said comparing means includes a graphic display of said light reflection parameter measurement made substantially simultaneously on two extremities of a patient while both extremities of a patient are in said raised, steady-state condition with a light reflection parameter measurement made substantially simultaneously on both extremities of a patient while both extremities of said patient are in said lowered, steady-state condition, and wherein said indicating means includes a scale adjacent to said graph display.

37. A device according to claim 31, wherein said comparing means includes means for subtracting said light reflection parameter measurement made substantially simultaneously on two extremities of a patient while both extremities of a patient are in a raised, steady-state condition from a light reflection parameter measurement made substantially simultaneously on both extremities of a patient while both extremities of a patient are in a lowered, steady-state condition, and wherein said indicating means includes a display of results of said subtraction.

38. A device in accordance with claim 31, further comprising:

calibrating means for calibrating the light sensor units for measuring the light reflection parameter.

39. A device according to claim 38, wherein said calibration means includes inanimate objects having known light reflection parameter.

40. A device according to claim 39, wherein said calibration means further includes means for maintaining said inanimate objects at a predetermined temperature approximate to a temperature of said patient.

* * * * *

UNITED STATES PATENT AND TRADEMARK OFFICE
CERTIFICATE OF CORRECTION

PATENT NO.     :     5,542,421

DATED     :     August 6, 1996

INVENTOR(S)     :     Frank H. ERDMAN

It is certified that error appears in the above-identified patent and that said Letters Patent is hereby corrected as shown below:

On the cover page:

[*] Notice: please delete "5,542,421" and insert therefor --5,365,924--.

Signed and Sealed this

Twelfth Day of November, 1996

*Attest:*

BRUCE LEHMAN

*Attesting Officer*     *Commissioner of Patents and Trademarks*